(12) United States Patent
Brush et al.

(10) Patent No.: US 8,378,115 B2
(45) Date of Patent: Feb. 19, 2013

(54) MONOMETHINE DYES

(75) Inventors: Charles K. Brush, Gold Canyon, AZ (US); Jianqin Liu, Brookfield, WI (US); Peter Czerney, Weimar (DE); Matthias Wenzel, Jena (DE)

(73) Assignee: Thermo Fisher Scientific (Milwaukee) LLC, Milwaukee, WI (US)

( * ) Notice: Subject to any disclaimer, the term of this patent is extended or adjusted under 35 U.S.C. 154(b) by 116 days.

(21) Appl. No.: 12/680,881

(22) PCT Filed: Sep. 30, 2008

(86) PCT No.: PCT/US2008/078277
§ 371 (c)(1),
(2), (4) Date: Jun. 16, 2010

(87) PCT Pub. No.: WO2009/046010
PCT Pub. Date: Apr. 9, 2009

(65) Prior Publication Data
US 2010/0285470 A1    Nov. 11, 2010

Related U.S. Application Data

(60) Provisional application No. 60/976,822, filed on Oct. 2, 2007.

(51) Int. Cl.
*C07D 419/00* (2006.01)
*C07D 417/00* (2006.01)
*G01N 33/566* (2006.01)
*C12Q 1/68* (2006.01)

(52) U.S. Cl. .......... 548/159; 544/368; 436/501; 435/6.1

(58) Field of Classification Search .................. None
See application file for complete search history.

(56) References Cited

U.S. PATENT DOCUMENTS
2010/0323453 A1   12/2010   Mao et al.

FOREIGN PATENT DOCUMENTS

| JP | 61-278191 | 12/1986 |
|----|-----------|---------|
| WO | 97/45539 A1 | 12/1997 |
| WO | 01/02558 A1 | 1/2001 |
| WO | 01/90253 A1 | 11/2001 |
| WO | 2005/033342 A1 | 4/2005 |
| WO | 2008/015415 A2 | 2/2008 |

OTHER PUBLICATIONS

Tolmachev et al. Zhurnal Obshchei Khimii (1963), 33:440-447.*
Almeida, P. et al "New amino and acetamido monomethine cyanine dyes for the detection of DNA in agarose gels" Bioorganic & Medical Chemistry. 2007, 15, 5537-5542 (epub. May 23, 2007), ISSN: 0968-0896.
Yarmoluk, S. M. et al "Studies of momomeric and homodimeric oxazolo[4,5-b] pyridinium cyanine dyes as fluorescent probes for nucleic acids visualization" Journal of Biochemical and Biophysical Methods. 2006, 68, 155-165, ISSN: 0165-022X.
Bianco, P.R. et al "Novel, Monomeric Cyanine Dyes as Reporters for DNA Helicase Activity" Journal of Fluorescence. 2007, 17(6), 671-685 (epub. Aug. 3, 2007), ISSN: 1053-0509.
Vitzthum, F. et al "Investigation on DNA intercalation and surface binding by SYBR Green I, its structure determination and methodological implications" Nucleic Acids Research. 2004, 32(12), e 103, ISSN: 0305-1048.
Written Opinion dated Apr. 6, 2009, Issued in International Application No. PCT/US2008/078277.
International Search Report Apr. 6, 2009, Issued in International Application No. PCT/US2008/078277.
Almeida, P. et al. "New amino and acetamido monomethine cyanine dyes for the detection of DNA in agarose gels" Bioorganic & Medical Chemistry. vol. 15 (2007), pp. 5537-5542.
Yarmoluk, S. M. et al. "Studies of monomeric and homodimeric oxazolo [4,5-b] pyridinium cyanine dyes as fluorescent probes for nucleic acids visualization" J. Biochem. Biophys, Methods vol. 68 (2006), pp. 155-165.
Bianco, P.R. et al. "Novel, Monomeric Cyanine Dyes as Reporters for DNA Helicase Activity" J. Fluoresc vol. 17 (2007), pp. 671-685.
Vitzthum, F. et al. "Investigation of DNA intercalation and surface binding by SYBR Green I, its structure determination and methodological implications" Nucleic Acids Research. vol. 32 (2004), No. 12 e103.
International Preliminary Report on Patentability Issued Apr. 7, 2010, mailed Apr. 15, 2010.
Extended European Search Report, dated May 6, 2011.
Shandura et al., Substituted xanthylocyanines. II Pyroninocyanines, Dyes and Pigments, Elsevier, 2005, 66:3, pp. 171-177.
El-Shishtawy, R.M. et al. "New amino and acetamido monomethine cyanine dyes for the detection of DNA in agarose gels" Bioorganic & Medical Chemistry. vol. 15 (2007), pp. 5537-5542.
Kovalska, V.B. et al. "Studies of monomeric and homodimeric oxazolo [4,5-b] pyridinium cyanine dyes as fluorescent probes for nucleic acids visualization" J. Biochem. Biophys, Methods vol. 68 (2006), pp. 155-165.
Xu, C. et al. "Novel, Monomeric Cyanine Dyes as Reporters for DNA Helicase Activity" J. Fluoresc vol. 17 (2007), pp. 671-685.
Zipper, H. et al. "Investigation of DNA intercalation and surface binding by SYBR Green I, its structure determination and methodological implications" Nucleic Acids Research. vol. 32 (2004), No. 12 e103.
Extended European Search Report EP11191414.9, mailed Nov. 16, 2012, 10 pages.
Communication EP08835988.0, mailed Nov. 22, 2012, 6 pages.

*Primary Examiner* — Kamal Saeed
*Assistant Examiner* — Nyeemah A Grazier
(74) *Attorney, Agent, or Firm* — Thompson Hine LLP

(57) ABSTRACT

Monomethine dyes that have no or minimal fluorescence in buffer or in the presence of single stranded DNA or RNA, but strongly fluoresce in the presence of double-stranded DNA. In one embodiment, the dye is useful in quantitative RT-PCR.

12 Claims, 11 Drawing Sheets

X=O,S, R= alkyl, aryl, aralkyl qRT-PCR with V02-07027 qRT-PCR with V02-07015

Melting Curve using V02-07027

MONOMETHINE DYES

This application claims priority to U.S. application Ser. No. 60/976,822, filed Oct. 2, 2007, and is hereby incorporated by reference in its entirety.

BACKGROUND

A polymethine dye is a dye having a linearly conjugated system with an odd number of methine (—CH=) groups, where the terminal heteroatoms N, O, or S, eventually are included in two terminal heterocycles $Het_1$ and $Het_2$. As described herein, polymethines are a delocalized π (pi) electron system, represented by at least in two equivalent formulas shown below:

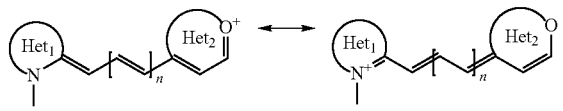

A monomethine dye has n=0, thus having a single —C= between the heterocycles. When n=1, the dye is a trimethine, and so on.

Numerous monomethine dyes are known. Some monomethine dyes have the characteristic of no or minimal fluorescence in buffer or in the presence of single stranded DNA (ssDNA) or RNA, but strong fluorescence in the presence of double-stranded DNA (dsDNA). Examples of such dyes, which are commercially useful because of this characteristic, include SYBR Green, Thiazole Orange, BOXTO, Eva Green, and LC Green. SYBR Green, the structure of which is shown below,

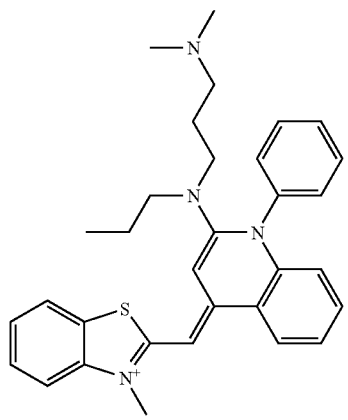 [SMILES: CCCN(CCCN(C)C)C1=C/C(=C\c2sc3ccccc3[n+]2C)c2ccccc2N1c1ccccc1]

is one the most commonly used fluorescent dyes.

Benzopyrylium monomethines are known, but none has the side chain needed for utility in fluorescence studies, and none has been used in dsDNA binding assays.

Other such dyes are desirable.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A having a benzthiazole moiety, and FIG. 2B having a benzoxazole moiety.

DETAILED DESCRIPTION

Compounds and their compositions, also referred to herein as dyes, are disclosed. The disclosed dyes have enhanced fluorescence, in some cases fluorescence comparable to commercially available dsDNA binding dyes. They have enhanced selective binding to double stranded DNA (dsDNA) compared to single stranded DNA (ssDNA), that is, they have minimal fluorescence in the absence of dsDNA and significance fluorescence in the presence of dsDNA. They have enhanced brightness, and are used to detect PCR amplicons in quantitative real time polymerase chain reaction (qRT-PCR). In embodiments, the dyes may exhibit affinity for RNA.

Figure 1:
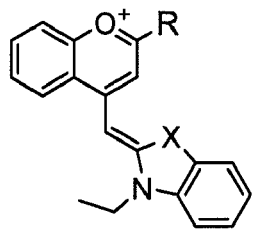
FIG. 1 shows the general structure of benzopyrylium monomethine compounds.

To produce such dyes, a series of monomethine compounds that include the benzopyrylium moiety were synthesized. The general chemical structure of the benzopyrylium monomethine compound is shown in FIG. 1; substitutions for R in addition to alkyl, aryl, and aralkyl are possible.

More specifically, these compounds have the formula

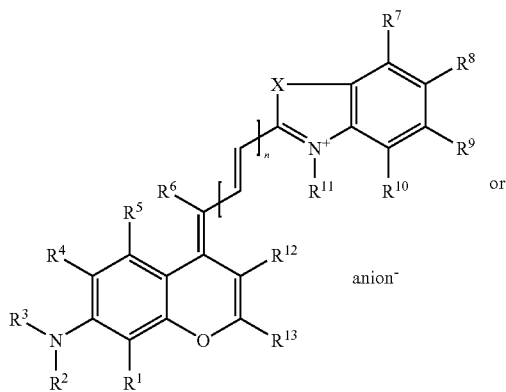

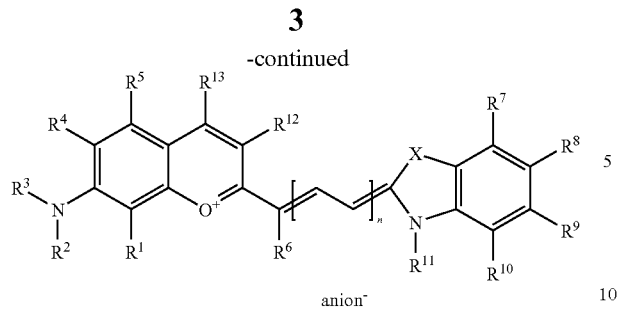

where each of $R^1$-$R^{10}$ and $R^{12}$ is independently H or a linear or branched hydrocarbon, optionally containing one or more heteroatoms;

$R^1$ and $R^2$, $R^2$ and $R^3$, $R^3$ and $R^4$, $R^4$ and $R^5$, $R^7$ and $R^8$, $R^8$ and $R^9$, $R^9$ and $R^{10}$ or $R^6$ and $R^{12}$ are substituents capable of forming an aliphatic chain or ring, or an aromatic ring;

$R^{11}$ is a linear or branched hydrocarbon, optionally containing one or more heteroatoms;

$R^{13}$ is selected from a linear or branched hydrocarbon that is saturated or unsaturated, optionally containing one or more heteroatoms, optionally containing a tetraalkylammonium group; aryl or pyrimidyl; or $NR^{14}R^{15}$ where $R^{14}$ and $R^{15}$ are the same or different and are independently H or a hydrocarbon, optionally containing one or more heteroatoms, optionally containing a tetraalkylammonium group, or $R^{14}$ and $R^{15}$ in combination complete a five, six, or seven membered saturated ring, optionally containing one or more heteroatoms, and optionally containing a quaternary ammonium group; or $R^{13}$ is a linker connecting the rest of the molecule to another benzopyrylium methine dye, forming a dimer dye structure. The dyes of the dimer may be the same or different.

X is selected from the group consisting of O, S, Se, $NR^{16}$ where $R^{16}$ is H or a hydrocarbon optionally containing one or more heteroatoms, and $CR^{17}R^{18}$ where $R^{17}$ and $R^{18}$ are the same or different and are independently a hydrocarbon optionally containing one or more heteroatoms, or in combination complete a five, six, or seven membered saturated ring, optionally containing one or more heteroatoms;

n is an integer from 0 to 3 inclusive; and anion is a counterion.

Figure 2A:
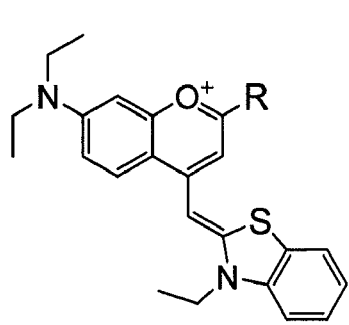
FIGS. 2A and 2B show the general structures of two classes of monomethine dyes.
Figure 2B:
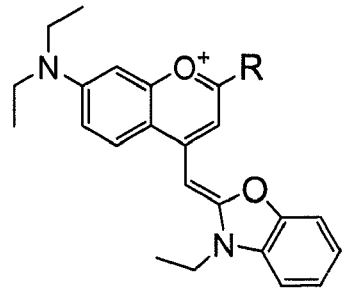
Figure 3:
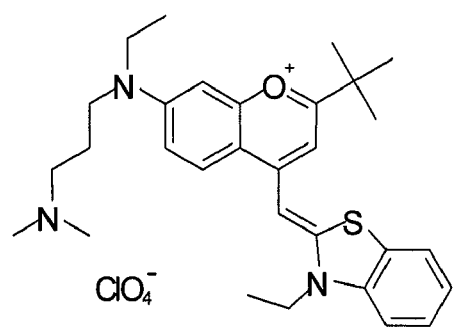
FIG. 3 shows the structure of one type of benzopyrylium monomethine dye.

The general structures of two classes of monomethine dyes is shown in FIGS. 2A and 2B; FIG. 2A shows a compound with a benzthiazole moiety, and FIG. 2B shows a compound with a benzoxazole moiety.

Benzopyrylium monomethine compounds were synthesized generally by condensation of an activated methyl group on the benzopyrylium moiety and an activated sulfide on the other heterocycle in the presence of a tertiary amine. An example of the reaction is shown below

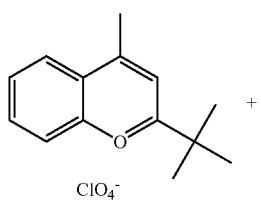

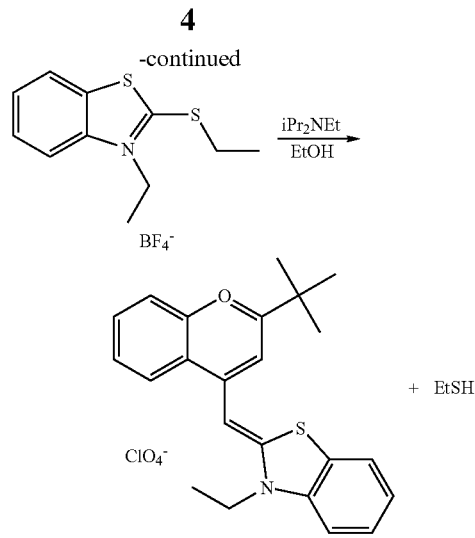

Synthesis and properties of representative compounds was as follows.

V02-07027

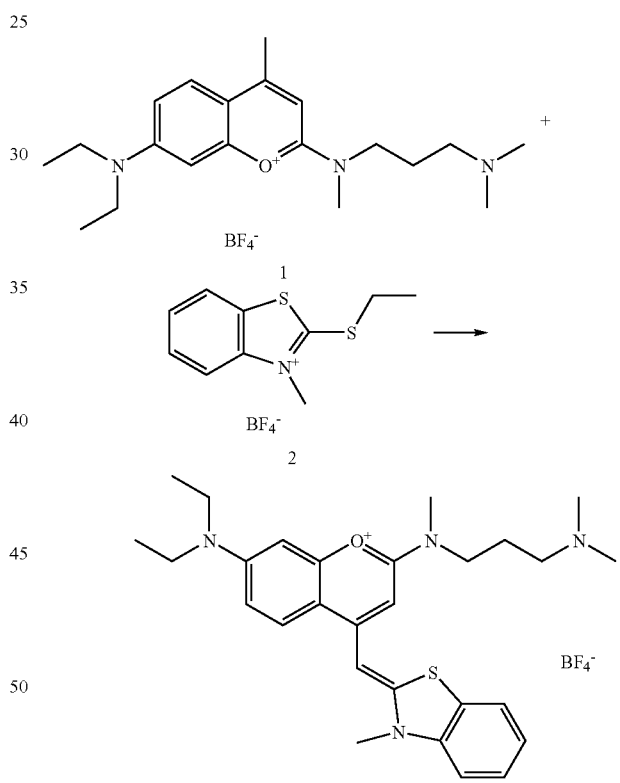

100 mg (240 μmol) benzopyrylium-salt 1 and 93 mg (312 μmol) of 2-(ethylthio)-3-methyl-1,3-benzothiazol-3-ium tetrafluoroborate 2 were mixed in 10 mL ethanol. Ethyldiisopropylamine (53 μL (312 μmol)) was added and the mixture was refluxed for two hours. The reaction mixture was then cooled and the ethanol was removed under vacuum. The yellow/brown residue was purified by column chromatography.

Yield: 40%
$C_{28}H_{37}N_4OS*BF_4$
M=564.50 g/mol
$\lambda_{max}$=477 nm (ethanol)=
$\epsilon$=60,000 L/mol*cm

V13-01184

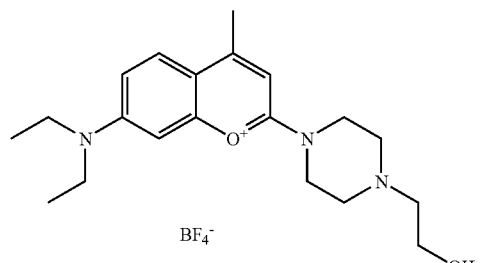

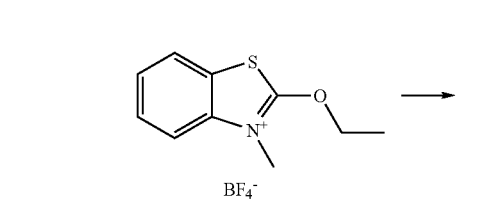

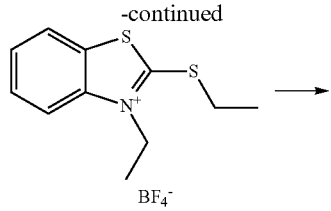

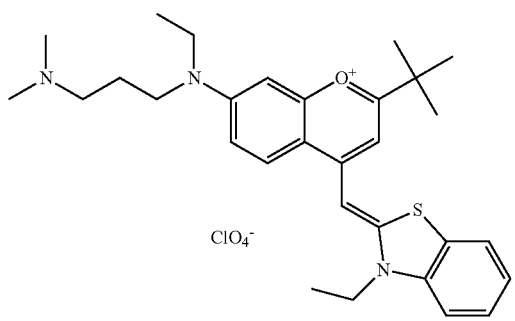

100 mg (286 μmol) benzopyrylium-salt and 87 mg (286 μmol) 2-(ethylthio)-3-ethyl-1,3-benzothiazol-3-ium tetrafluoroborate were dissolved in 10 mL ethanol, followed by addition of 49 μL (286 μmol) ethyl-diisopropylamine. The mixture was refluxed for about one hour, cooled to ambient temperature (about 20° C. to about 22° C.), then the ethanol was removed under vacuum. The brown residue was purified by column chromatography.

Yield: 20%

$C_{30}H_{40}N_3OS*ClO_4$

M=590.12 g/mol $\lambda_{max}$=522 nm (ethanol)

$\epsilon$=50,000 L/mol*cm

V13-01026

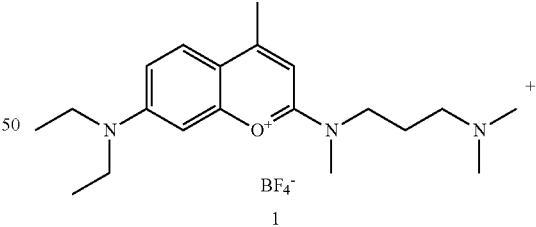

100 mg (232 μmol) benzopyrylium-salt 1 and 93 mg (312 μmol) of 2-(ethylthio)-3-methyl-1,3-benzothiazol-3-ium tetrafluoroborate 2 were mixed in 10 mL ethanol. Ethyldiisopropylamine (53 μL (312 μmol)) was added and the mixture was refluxed for two hours. The reaction mixture was then cooled and the ethanol was removed under vacuum. The yellow/brown residue was purified by column chromatography.

Yield: 42

$C_{28}H_{35}N_4O_2S*BF_4$

M=578.48 g/mol $\lambda_{max}$=481 nm (ethanol)

$\epsilon$=83,000 L/mol*cm

V02-07015

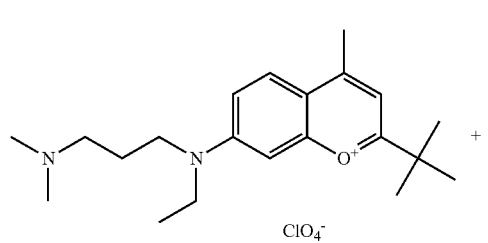

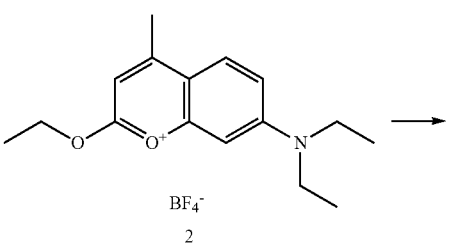

100 mg (232 μmol) benzopyrylium-salt 1 and 83 mg (232 μg) benzopyrylium-salt 2 were mixed in 10 mL ethanol. Ethyldiisopropylamine (40 μL (232 μmol)) was added and the mixture was refluxed for one hour. After cooling to ambient temperature (about 20° C. to about 22° C.), the resulting red precipitate was filtered off, washed with diethylether, and dried.

Yield: 15%
$C_{34}H_{37}N_4O_2*BF_4$
M=630.57 g/mol
$\lambda_{max}$=585 nm (ethanol)
$\epsilon$=50,000 L/mol*cm
V02-06187

100 mg (264 μmol) benzopyrylium-salt 1 and 82 mg (264 μmol) 2-(ethylthio)-3-ethyl-1,3-benzothiazol-3-ium tetrafluoroborate 2 were mixed in 10 mL ethanol. Ethyldiisopropylamine (40 μL (232 μmol)) was added and the mixture was refluxed for one hour, followed by addition of 80 mg (528 μmol) sodium iodide. After cooling to ambient temperature (about 20° C. to about 22° C.), the resulting orange precipitate was filtered off, washed with diethylether, and dried.

Yield: 25%
$C_{29}H_{29}N_2OS*I$
M=580.53 g/mol
$\lambda_{max}$=550 nm (ethanol)
$\epsilon$=55,000 L/mol*cm
V02-06188

100 mg (264 μmol) benzopyrylium-salt 1 and 78 mg (264 μmol) 2-(ethylthio)-3-ethyl-1,3-benzoxazol-3-ium tetrafluoroborate 2 were mixed in 10 mL ethanol. Ethyldiisopropylamine (40 μL (232 μmol)) was added and the mixture was refluxed for one hour followed by addition of 80 mg (528 μmol) sodium iodide. After cooling to ambient temperature (about 20° C. to about 22° C.), the resulting orange precipitate was filtered off, washed with diethylether, and dried.

Yield: 15%
$C_{29}H_{29}N_2O_2*BF_4$
M=524.36 g/mol
$\lambda_{max}$=520 nm (ethanol)
$\epsilon$=55,000 L/mol*cm

V02-07108

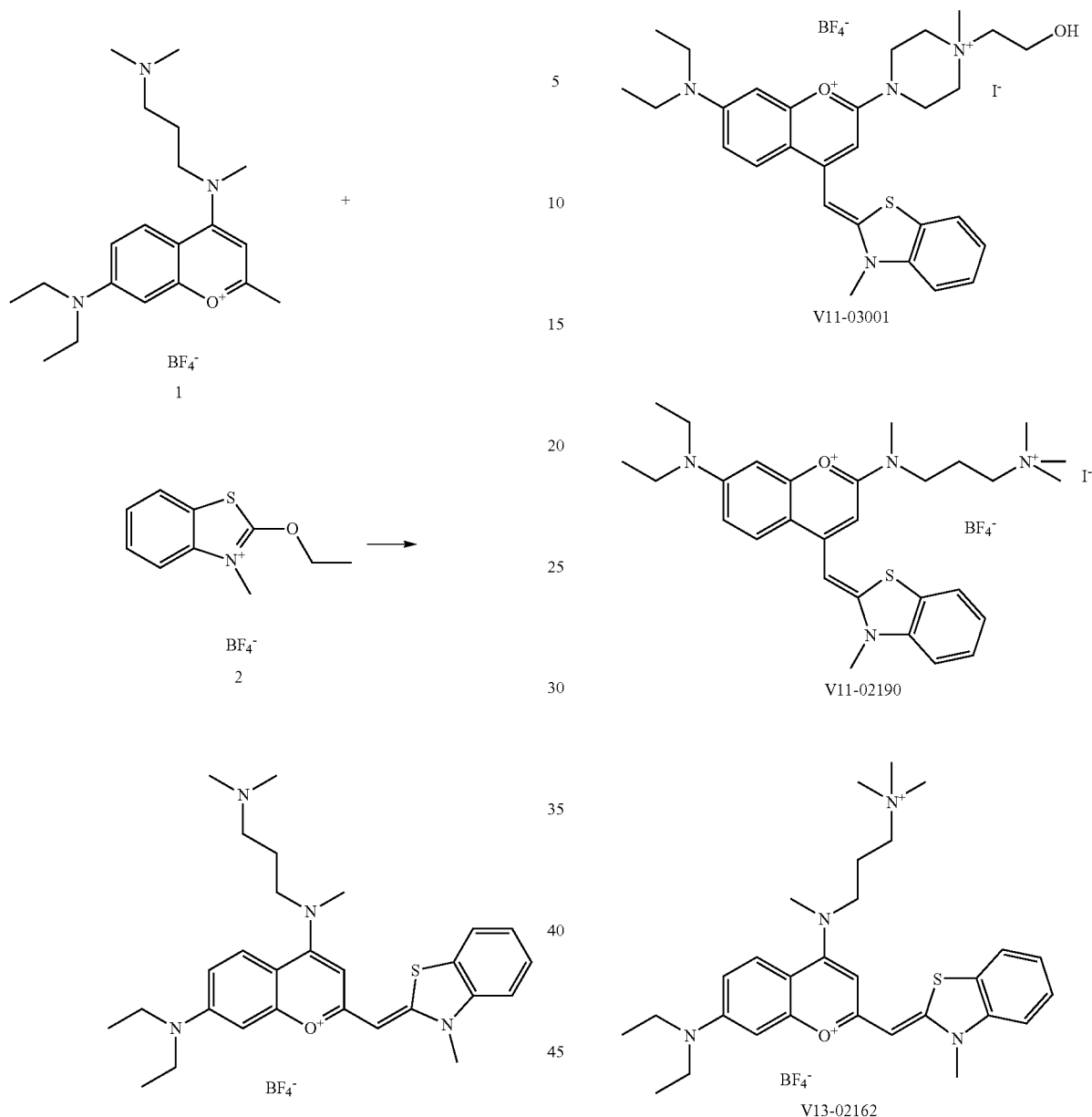

100 mg (240 μmol) benzopyrylium-salt 1 and 93 mg (312 μmol) of 2-(ethylthio)-3-methyl-1,3-benzothiazol-3-ium tetrafluoroborate 2 were mixed in 10 mL ethanol. Ethyldiisopropylamine (53 μL (312 μmol)) was added and the mixture was refluxed for two hours. The reaction mixture was then cooled and the ethanol was removed under vacuum. The yellow/brown residue was purified by column chromatography.

Yield: 40%

$C_{28}H_{37}N_4OS*BF_4$

M=564.50 g/mol $\lambda_{max}$=498 nm (ethanol)

$\epsilon$=50,000 L/mol*cm

In embodiments, the monomethine compounds may also include a tetralkylammonium and/or quaternary ammonium group. Examples of such compounds include Side chains useful for dsDNA binding, such as dimethylaminopropylmethylamine and analogues that provide a positive charge at the pH used in assays, were appended to the general dye.

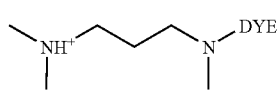

The resulting structures are grouped as Groups A, B, C, D, and E, shown below. Substituents for X, R7, R9, R10, R12, and R13 are shown in Table 1 below.

In embodiments, the monomethine compounds may also include dimers of the disclosed structures. Examples of such compounds include

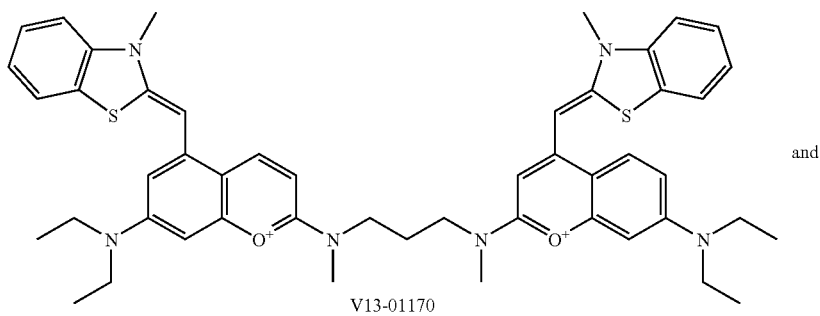

V13-01170 and

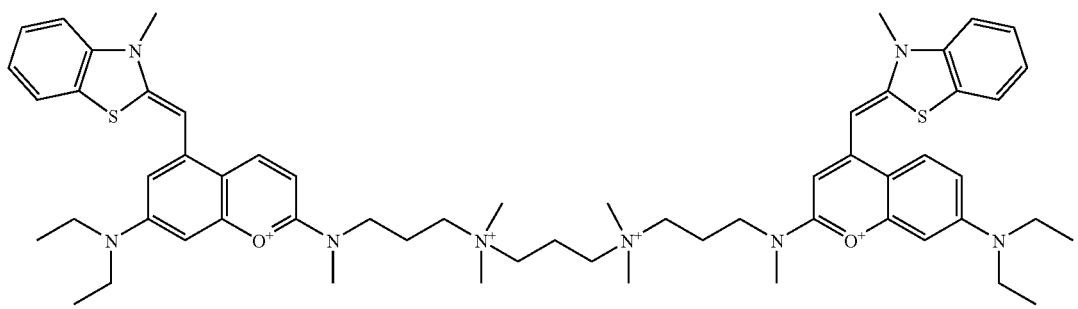

These compounds were dissolved in a biocompatible excipient, such as a buffer, and were evaluated in assays for fluorescence in the presence of ssDNA (40mer ssDNA), and in the presence of two kinds of dsDNA (40mer dsDNA and λDNA), as explained below.

Stock solutions (8 mM) of each dye were prepared by dissolving each compound in dimethylsulfoxide (DMSO). Stock dye solutions were diluted to a desired concentration in tris-EDTA (TE) buffer (10 mM Tris, 1 mM EDTA, pH 8.0) immediately prior to use.

Stock solutions of λDNA and 40mer synthetic oligonucleotides (dsDNA and ssDNA), each at a concentration of 40 μM, were prepared in TE buffer. All DNA concentrations described are in base pairs of nucleotides. The DNA stock solutions were diluted to a desired concentration in TE buffer before being mixed with diluted dye solutions.

Absorption spectra of the each dye alone (8 μM solutions in TE buffer) were measured on a Perkin Elmer LS55 fluorimeter. Absorption spectra of each dye-DNA complex were obtained by incubating 8 μM dye with 8 μM DNA in TE buffer for ten minutes. Optical densities were determined at the absorbance maxima and the extinction coefficients were calculated using Beer's law.

Fluorescence enhancement measurements of each dye were obtained by incubating dyes with λDNA, 40mer dsDNA, or 40mer ssDNA at a final concentration of 0.8 μM dye and 3.2 μM DNA for one minute. Fluorescence scans of the samples were performed with excitation wavelengths corresponding to the absorption maxima of the dyes. The resulting fluorescence intensities were compared to fluorescence intensities of Thiazole Orange (TO) and a compound equivalent to SYBR Green without the side chain (V02-06101), shown below,

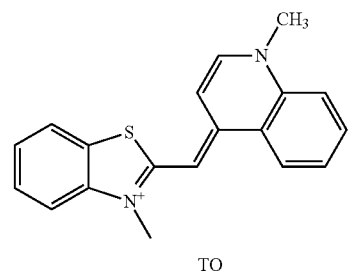

TO

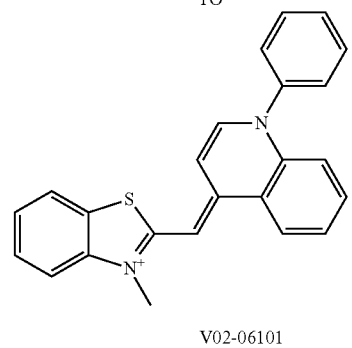

V02-06101 binding to λDNA, 40mer dsDNA, or 40mer ssDNA at a final concentration of 0.8 μM TO and 3.2 μM DNA for one minute, the same as for the tested dyes. The discrimination ratio between dsDNA and ssDNA was calculated by comparing the fluorescence intensities.

Final candidate compounds were then synthesized with the dimethylaminopropyl)methylamine side chain. A preliminary evaluation of these candidate compounds was conducted assessing fluorescence upon binding to the 240mer PCR amplicon or λ DNA. The most promising candidates were tested in quantitative real time polymerase chain reactions (qRT-PCR) on a commercially available instrument, using either commercially available mastermixes of reagents or individually prepared reagents.

Results for the disclosed dyes were evaluated in comparison to the following parameters of the known dye, SYBR Green:

absorption ±3 nm of SYBR Green ($\lambda_{max}$ (abs)=494 nm)
emission ±3 nm of SYBR Green ($\lambda_{max}$ (em)=524 nm)
extinction coefficient ($\epsilon$) not less than 68,000 (SYBR Green $\epsilon$=73,000)
ratio of fluorescence with dsDNA to ssDNA 25:1
fluorescence≧SYBR Green
compatibility with same buffers used with SYBR Green
no inhibition of PCR.

Results for fluorescence induced by benzopyrylium monomethine dyes binding to dsDNA are shown in Table 1.

Figure 4A:
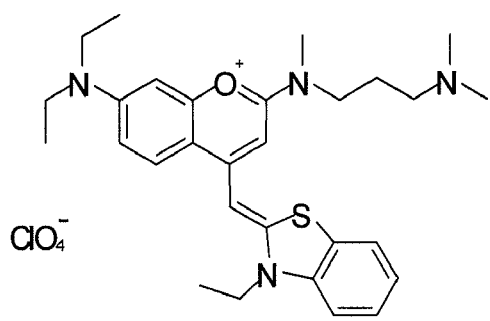
FIGS. 4A, 4B, and 4C show the structure of other types of benzopyrylium monomethine dyes.
Figure 4B:
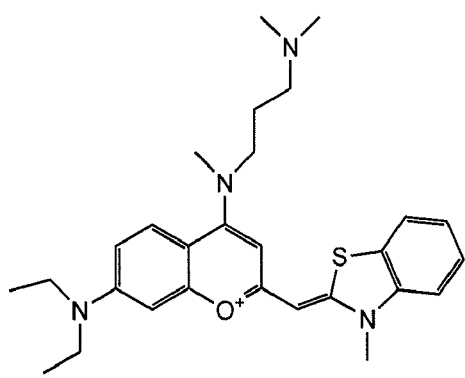
Figure 4C:
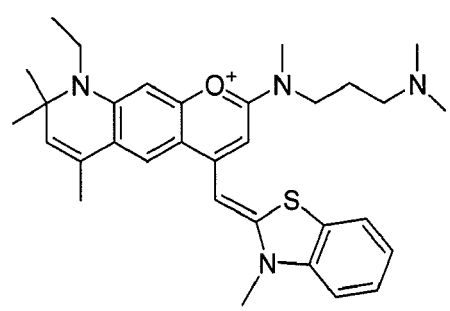
Figure 5A:
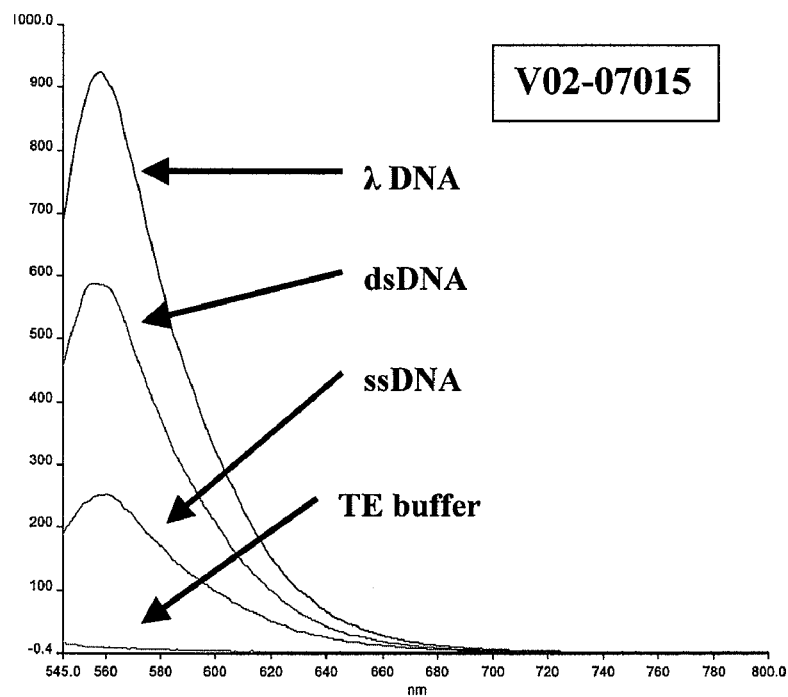
FIG. 5A shows the fluorescent spectra of V02-07015.
Figure 5B:
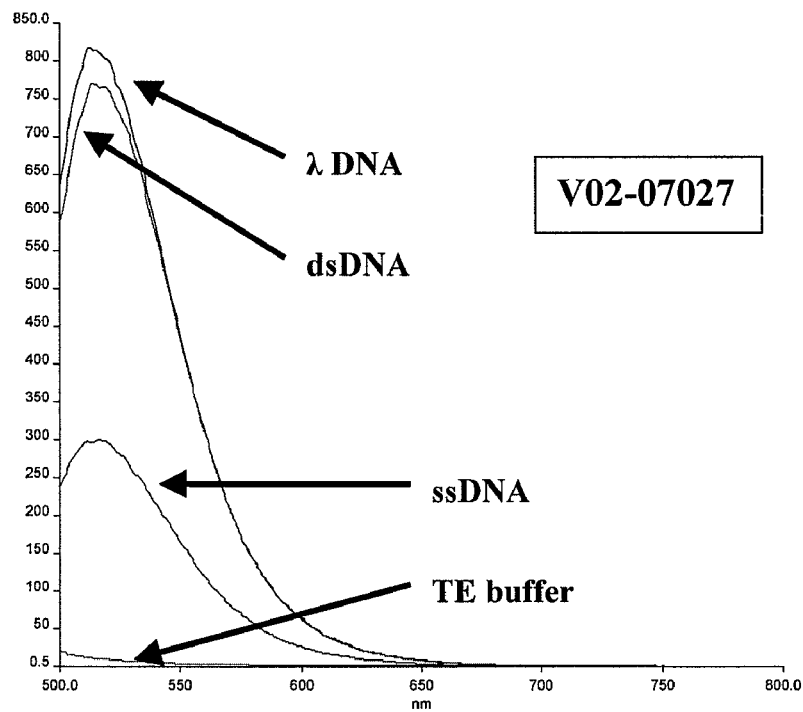
FIG. 5B shows the fluorescent spectra of V02-07027.
Figure 5C:
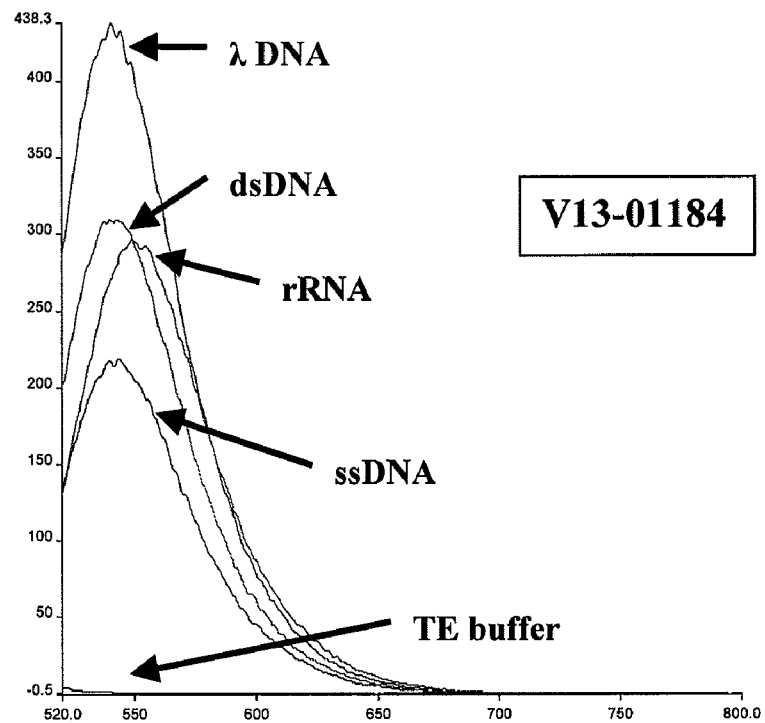
FIG. 5C shows the fluorescent spectra of V13-01184.
Figure 5D:
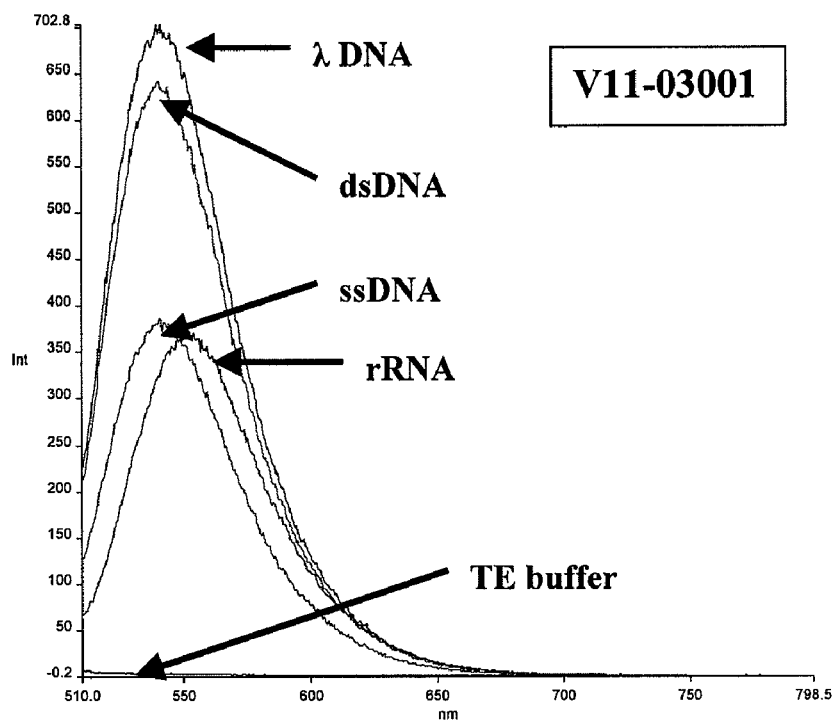
FIG. 5D shows the fluorescent spectra of V11-03001.

| Dye | Group | X | $R_7$ | $R_9$ | $R_{10}$ | $R_{12}$ | $R_{13}$ | Fluorescence $\lambda$ DNA/ssDNA | Fluorescence relative to TO |
|---|---|---|---|---|---|---|---|---|---|
| Thiazole Orange (TO) | A | | | $CH_3$ | H | $CH_3$ | | 3.3 | 1 |
| V02-06101 | A | | | Ph | H | $CH_3$ | | 4.1 | 0.8 |
| SYBR Green | A | | | Ph | $(CH_3CH_2CH_2)N(CH_2CH_2CH_2N(CH_3)_2)$ | $CH_3$ | | 8.3 | 10.6 |
| EVA Green | ? | | | | | | | 4.2 | 5.7 |
| V02-06124 | B | S | $(CH_3CH_2)_2N$ | | $C(CH_3)_3$ (t-Bu) | $CH_2CH_3$ | | 1.6 | 0.5 |
| V02-06136 | B | O | $(CH_3CH_2)_2N$ | | $C(CH_3)_3$ (t-Bu) | $CH_2CH_3$ | | 1 | 0.17 |
| V02-06132 | B | S | $OCH_3$ | | Ph | $CH_2CH_3$ | | None | None |
| V02-06135 | B | O | $OCH_3$ | | Ph | $CH_2CH_3$ | | None | None |
| V02-06187 | B | S | $(CH_3CH_2)_2N$ | | Ph | $CH_2CH_3$ | | 6.7 | 0.7 |
| V02-06188 | B | O | $(CH_3CH_2)_2N$ | | Ph | $CH_2CH_3$ | | 1.5 | 0.6 |
| V02-07015 | B | S | $(CH_3CH_2)N(CH_2CH_2CH_2N(CH_3)_2)$ | | $C(CH_3)_3$ (t-Bu) | $CH_2CH_3$ | | 3.7 | 4.0 |
| V02-07027 | B | S | $(CH_3CH_2)_2N$ | | $(CH_3)N(CH_2CH_2CH_2N(CH_3)_2)$ | $CH_3$ | | 2.8 | 3.6 |
| V02-06123 | C | N | $(CH_3)_2N$ | | $C(CH_3)_3$ (t-Bu) | Ph | | None | None |
| V02-06144 | C | N | $OCH_3$ | | Ph | $(CH_2)_3OCOCH_3$ | | None | None |
| V02-06139 | C | O | $(CH_3CH_2)_2N$ | | $C(CH_3)_3$ (t-Bu) | $C(CH_3)_3$ (t-Bu) | | None | None |
| V13-01026 | D | | $(CH_3CH_2)_2N$ | | $(CH_3)N(CH_2CH_2CH_2N(CH_3)_2)$ | R14 $CH_3$ | | 1.4 | 0.9 |
| V13-01035 | E | | $(CH_3CH_2)_2N$ | | $(CH_3)N(CH_2CH_2CH_2N(CH_3)_2)$ | | | 1.1 | 0.9 |
| V13-01184 | B | S | $(CH_3CH_2)_2N$ | | 4-hydroxyethylpiperazinyl | $CH_3$ | | 6.1 | 5.3 |
| V02-07108 | F | S | $(CH_3CH_2)_2N$ | | $(CH_3)N(CH_2CH_2CH_2N(CH_3)_2)$ | $CH_3$ | | 1.8 | 3.1 |
| V11-03001 | B | S | $(CH_3CH_2)_2N$ | | 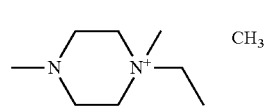 | $CH_3$ | | | |
| V12-02144 | B | S | (see FIG. 4C) | | $(CH_3)N(CH_2CH_2CH_2N(CH_3)_2)$ | $CH_3$ | | 2.8 | 3.6 |

-continued
| Dye | Group | X | R₁ | R₇ | R₉ | R₁₀ | R₁₄ |
|---|---|---|---|---|---|---|---|
| V13-01026 | G | | $(CH_3CH_2)_2N$ | $(CH_3CH_2)_2N$ | | $(CH_3)N(CH_2CH_2CH_2N(CH_3)_2)$ | $CH_3$ |
| V13-01035 | H | | | $(CH_3CH_2)_2N$ | | $(CH_3)N(CH_2CH_2CH_2N(CH_3)_2)$ | |
| V13-01170 | I (dimer) | S | | $(CH_3CH_2)_2N$ | | | |
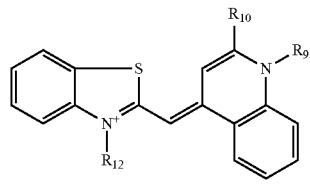
Group A
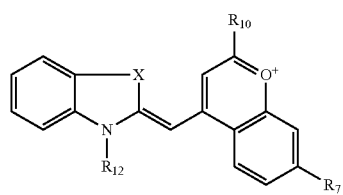
Group B
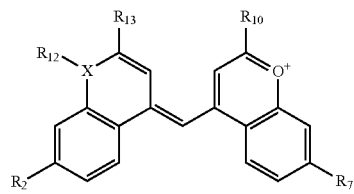
Group C
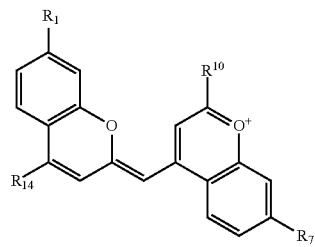
Group D
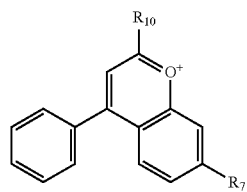
Group E
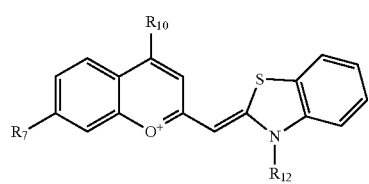
Group F

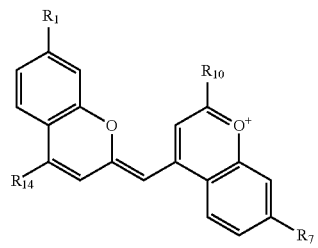
GroupG
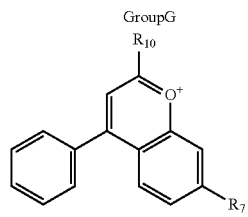
Group H
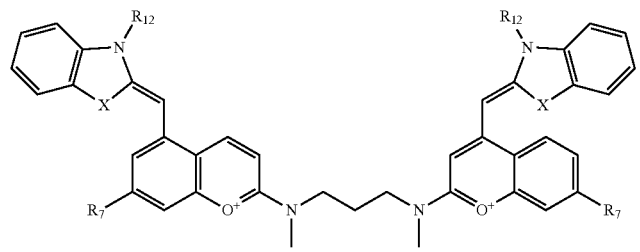
Group I
Each of the benzopyrylium monomethines of FIGS. 2A, 2B, 3, 4A, 4B, and 4C exhibited strong fluorescence in the presence of dsDNA; some approached the fluorescence of SYBR Green. The compound shown in FIG. 3 had about 50% of the fluorescence of SYBR Green in the presence of dsDNA. It was evaluated in qRT PCR.
Compounds V02-07015, V13-01184, V13-01170, V02-07108, V11-03001, V02-07027 and V12-02144 were evaluated.
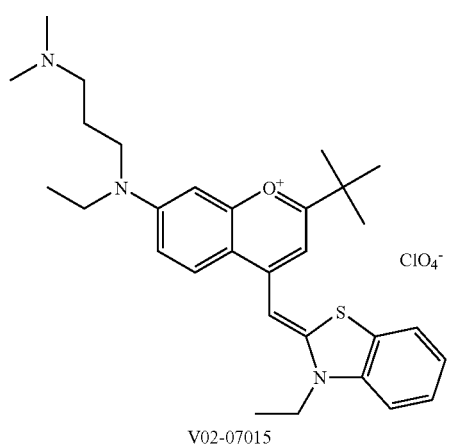
V02-07015
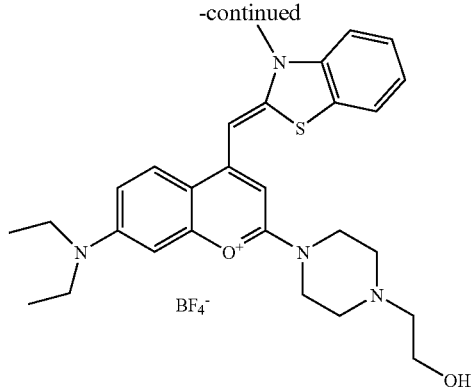
V13-01184
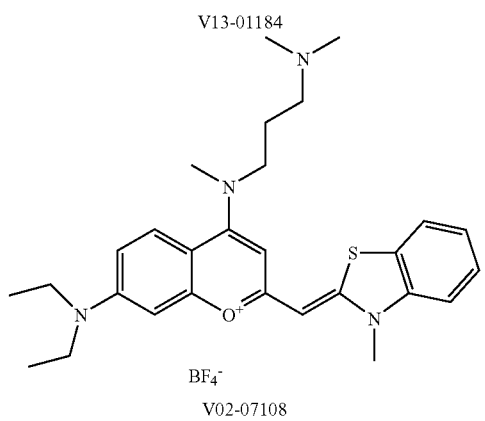
V02-07108

-continued

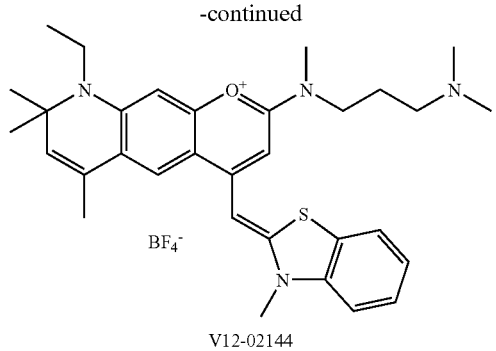

V12-02144

Among these compounds, V13-01184, V11-03001, V02-07015 and V02-07027 showed increased fluorescence in the presence of DNA compared to other compounds, as shown in FIGS. 5A-5D, with the dyes in the presence of TE buffer, 40mer ssDNA, 40mer dsDNA, λ DNA, and rRNA, as indicated. The fluorescence intensities were 4 to 8 times higher than that for the reference Thiazole Orange Dye (Table 3). Dye V13-01184, V11-03001, V02-07015 and V02-07027 also showed discrimination between dsDNA and ssDNA. The fluorescence intensities in the presence of dsDNA were 1.4-3.7 times higher than corresponding intensities in the presence of ssDNA (Table 3). It was noted that substitution of long amino side chain on the R10 or R7 position in Group B dyes increased the fluorescence intensity in the presence of DNA (for example dye V02-07015 and V02-07027). Substitution the R10 group with pyperazine ethanol side chain increased the fluorescence significantly (dye V13-01184 and V11-03001). Among all the dyes studied, dye V11-03001 showed the strongest fluorescence enhancement, which was comparable to that for SYBR Green dye.

TABLE 1

Spectral characterization

| | Ethanol | | TE Buffer | |
|---|---|---|---|---|
| Dye | $\lambda_{ex}$ (nm) | $\epsilon$ | $\lambda_{ex}$ (nm) | $\epsilon$ |
| TO | 501 | 77,000 | 501 | 52,773 |
| 101 | 508 | 96,000 | 508 | 67,750 |
| SYBR | — | — | 494 | 73,000 |
| EVA | — | — | 471 | — |
| V02-06124 | 530 | 85,000 | 515 | 46,625 |
| V02-06136 | 499 | 72,000 | 492 | 35,925 |
| V02-06132 | 488 | 43,000 | 480 | 18,850 |
| V02-06135 | 464 | 43,000 | | |
| V02-06187 | 550 | 55,000 | 524 | 19,668 |
| V02-06188 | 520 | 58,000 | 499 | 20,444 |
| V02-07015 | 522 | 50,000 | 515 | 37,365 |
| V02-07027 | 477 | 60,000 | 475 | 39,987 |
| V02-06123 | 590 | 89,000 | 560 | 39,750 |
| V02-06144 | 538 | 35,000 | 520 | 9,862 |
| V02-06139 | 622 | 116,000 | 583 | 31,300 |
| V13-01026 | 585 | 48,000 | 543 | 25,013 |
| V13-01035 | 452 | 22,000 | 453 | 19,651 |
| V13-01184 | 480 | 83,000 | 455 | 40,321 |
| V13-01170 | 455 | 95,000 | 441 | 51,644 |
| V10-02067 | 507 | 96,000 | 490 | 26,400 |
| V02-07108 | 498 | 46,000 | 496 | 27,418 |
| V12-02144 | 492 | 49,000 | 484 | 28,355 |
| V11-03001 | 490 | 95,000 | 487 | 65,269 |
| V11-02190 | 481 | 25,600 | 477 | 16,940 |

TABLE 2

Absorption spectra characterization in the presence of DNA

| | 40-mer ds-DNA | | λ DNA | | 40-mer ss-DNA | |
|---|---|---|---|---|---|---|
| Dye | $\lambda_{ex}$ (nm) | $\epsilon$ | $\lambda_{ex}$ (nm) | $\epsilon$ | $\lambda_{ex}$ (nm) | $\epsilon$ |
| TO | 502 (485s) | 32,613 | 504 (485s) | 37,813 | 475 (499s) | 26,762 |
| 101 | 508 | 52,663 | 509 | 52,050 | 507 | 43,175 |
| SYBR | 494 | 69,225 | 492 | 67,785 | 494 | 56,588 |
| EVA | | | 473 | | — | |
| V02-06124 | 521 | 22,063 | 526 | 23,525 | 509 | 26,700 |
| V02-06136 | 492 | 29,450 | 494 | 31,763 | 487 | 25,138 |
| V02-06132 | 488 | 14,800 | 494 | 19,950 | 487 | 12,813 |
| V02-06135 | | | | | | |
| V02-06187 | 529 (560s) | 15,800 | 531 (560s) | 21,726 | 529 (560s) | 17,329 |
| V02-06188 | 508 (530s) | 19,755 | 508 (530s) | 21,679 | 508 (530s) | 24,026 |
| V02-07015 | 516 | 20,520 | 525 | 23,896 | 503 | 20,552 |
| V02-07027 | 478 | 24,519 | 480 | 39,148 | 456 | 27,605 |
| V02-06123 | 566 | 18,525 | 561 | 28,750 | 561 | 15,813 |
| V02-06144 | 536 | 5,650 | 550 | 10,425 | 525 | 5,900 |
| V02-06139 | 583 | 27,800 | 583 | 28,588 | 588 | 25,800 |
| V13-01026 | 550 (593s) | 25,110 | 545 (593s) | 22,714 | 550 (593s) | 23,555 |
| V13-01035 | 455 | 17,441 | 455 | 16,351 | 455 | 17,595 |
| V13-01184 | 476 | 32,935 | 481 | 43,266 | 443 | 32,557 |
| V13-01170 | 430 | 53,637 | 427 | 55,540 | 440 | 50,398 |
| V10-02067 | 495 | 22,142 | 495 | 22,345 | 493 | 21,699 |
| V02-07108 | 468 | 18,340 | 496 | 22,879 | 475 | 18,585 |
| V12-02144 | 488 | 22,356 | 492 | 33,049 | 448 | 19,731 |
| V11-03001 | 489 | 41,096 | 489 | 55,290 | 489 | 30,256 |
| V11-02190 | 485 | 15,024 | 485 | 17,100 | 485 | 11,810 |

TABLE 3

Fluorescence spectral characterization in the presence of DNA

| Dye | 40-mer ds-DNA $\lambda_{em}$ (nm) | λ DNA $\lambda_{em}$ (nm) | Ratio ds/ss | λ DNA/ss | Relative Fluorescent Intensity 40-mer ds-DNA | λ DNA |
|---|---|---|---|---|---|---|
| TO | 530 | 530 | 3.5 | 5.6 | 1.0 | 1.0 |
| 101 | 535 | 535 | 2.5 | 4.1 | 0.5 | 0.8 |
| SYBR | 524 | 524 | 7.5 | 8.3 | 15.0 | 10.6 |
| EVA | | 526 | 3.3 | 4.2 | 9.0 | 5.7 |
| V02-06124 | 568 | 568 | 1.2 | 1.6 | 0.3 | 0.5 |
| V02-06136 | 533 | 533 | 1.8 | 1 | 0.3 | 0.17 |
| V02-06187 | 610 | 610 | 2.1 | 5.2 | 0.5 | 0.7 |
| V02-06188 | 580 | 580 | 1.5 | 2 | 0.6 | 0.6 |
| V02-07015 | 558 | 558 | 2.3 | 3.7 | 4.0 | 4.0 |
| V02-07027 | 515 | 515 | 2.6 | 2.8 | 5.3 | 3.6 |
| V13-01026 | 635 | 635 | 0.7 | 1.4 | 1.0 | 0.9 |
| V13-01035 | 540 | 540 | 1.2 | 1.1 | 1.1 | 0.6 |
| V13-01184 | 540 | 540 | 1.4 | 2.0 | 6.1 | 5.3 |
| V02-07108 | 569 | 564 | 1.4 | 1.9 | 3.5 | 3.1 |
| V12-02144 | 548 | 546 | 2.1 | 2.0 | 2.7 | 1.7 |
| V11-03001 | 540 | 540 | 1.7 | 1.8 | 11.1 | 8.7 |
| V11-02190 | 520 | 532 | 1.9 | 3.1 | 1.7 | 1.9 |

Dyes were investigated for RNA binding, some of which showed fluorescence enhancement in the presence of rRNA. Dyes V13-01184 and V11-03001 showed significant fluorescence enhancement when bound with RNA. V11-03001 showed the brightest fluorescence among all tested dyes and also showed a 12 nm red shift between RNA and DNA binding. The spectral properties are provided in Tables 4 and 5.

TABLE 4

Spectral characterization of the dyes in the presence of DNA/RNA

| Dye | 40-mer ds-DNA $\lambda_{ex}$ (nm) | ε | 40-mer ss-DNA $\lambda_{ex}$ (nm) | ε | rRNA $\lambda_{ex}$ (nm) | ε |
|---|---|---|---|---|---|---|
| TO | 502 (485s) | 32,613 | 475 (499s) | 26,762 | | |
| SYBR | 494 | 69,225 | 494 | 56,588 | | |
| V02-07015 | 516 | 20,520 | 503 | 20,552 | | |
| V02-07027 | 478 | 24,519 | 456 | 27,605 | | |
| V02-06132 | 488 | 14,800 | 494 | 19,950 | 475 | 24,235 |
| V13-01184 | 476 | 32,935 | 443 | 32,577 | 442 | 28,940 |
| V13-01170 | 430 | 53,637 | 440 | 50,398 | 431 | 54,951 |
| V10-02067 | 495 | 22,142 | 495 | 22,345 | 495 | |
| V02-07108 | 468 | 18,348 | 475 | 18,585 | 479 | 21,140 |
| V12-02144 | 488 | 22,356 | 448 | 19,731 | 449 (493 shoulder) | 21,445 |
| V11-03001 | 489 | 41,096 | 489 | 30,256 | 552 | 36,499 |
| V11-02190 | 485 | 15,024 | 485 | 11,810 | 485 | 13,134 |

TABLE 5

Fluorescence characterization of dyes in the presence of DNA

| Dye | 40-mer ss-DNA $\lambda_{em}$ (nm) | 40-mer ds-DNA $\lambda_{em}$ (nm) | rRNA $\lambda_{em}$ (nm) | Ratio rRNA/ss | rRNA/ds |
|---|---|---|---|---|---|
| TO | 535 | 530 | 533 | 2.3 | 0.8 |
| SYBR | 533 | 524 | 525 | 1.0 | 0.3 |
| V02-07015 | 561 | 558 | | | |
| V02-07027 | 514 | 515 | | | |
| V13-01184 | 544 | 540 | 549 | 1.4 | 1.0 |
| V02-07108 | 572 | 565 | 568 | 1.1 | 0.8 |
| V12-02144 | 553 | 546 | 551 | 1.5 | 0.7 |
| V11-03001 | 540 | 540 | 552 | 1.0 | 0.6 |
| V11-02190 | 516 | 520 | 516 | 1.4 | 0.7 |

Real-time PCR was performed in 25 µL volumes on a Stratagene® MX3005p (Stratagene, La Jolla Calif.). The following PCR protocol was used to amplify a 94 base pair (bp) product from the Human GAPDH gene; 95° C.×10 min, followed by 45 cycles of 95° C.×20 sec, 60° C.×20 sec, and 72° C.×22 sec (data collected at 72° C. step). Each amplification reaction (25 µL) included 10 ng of Human Genomic DNA template (Sigma), 200 µM of each dNTP, 3 mM $MgCl_2$, 50 mM KCL, 10 µm EDTA, 10 mM Tris, 5% DMSO, 70 nM of both forward (5' ACA GTC AGC CGC ATC TTC TT) and reverse (5' ACG ACC AAA TCC GTT GAC TC) primers, and 0.625 units of Taq DNA polymerase (Thermo Scientific). The dyes were included at varying concentrations. ABsolute™ QPCR SYBR® Green master mix (Thermo Scientific) was used for amplification when SYBR® Green I was required as the indicator. No template control (NTC) reactions without DNA were also included. The fluorescent signal was monitored in the following five channels (nm excitation/nm emission): 492/516, 535/555, 545/568, 585/610, and 635/665. Presence of amplicon was determined using post-amplification melt-curve analysis (95° C.×60 sec×1 cycle, 60° C.×30 sec×1 cycle followed by 95° C.×30 sec (with continuous data collection during ramping)) and agarose gel electrophoresis. All reactions were performed in triplicate but are shown as a single curve (average of the three individual reactions).

To evaluate the ability of the dyes to detect PCR products in real-time, a 94 bp fragment of the human GAPDH gene was amplified from 10 ng of human genomic DNA. Each of dyes V02-07027 and V02-07015 at 80 ng, 120 ng, and 160 ng were included in 25 µL amplification reactions (previous experiments were used to narrow the testing range of the dyes).

Figure 6:
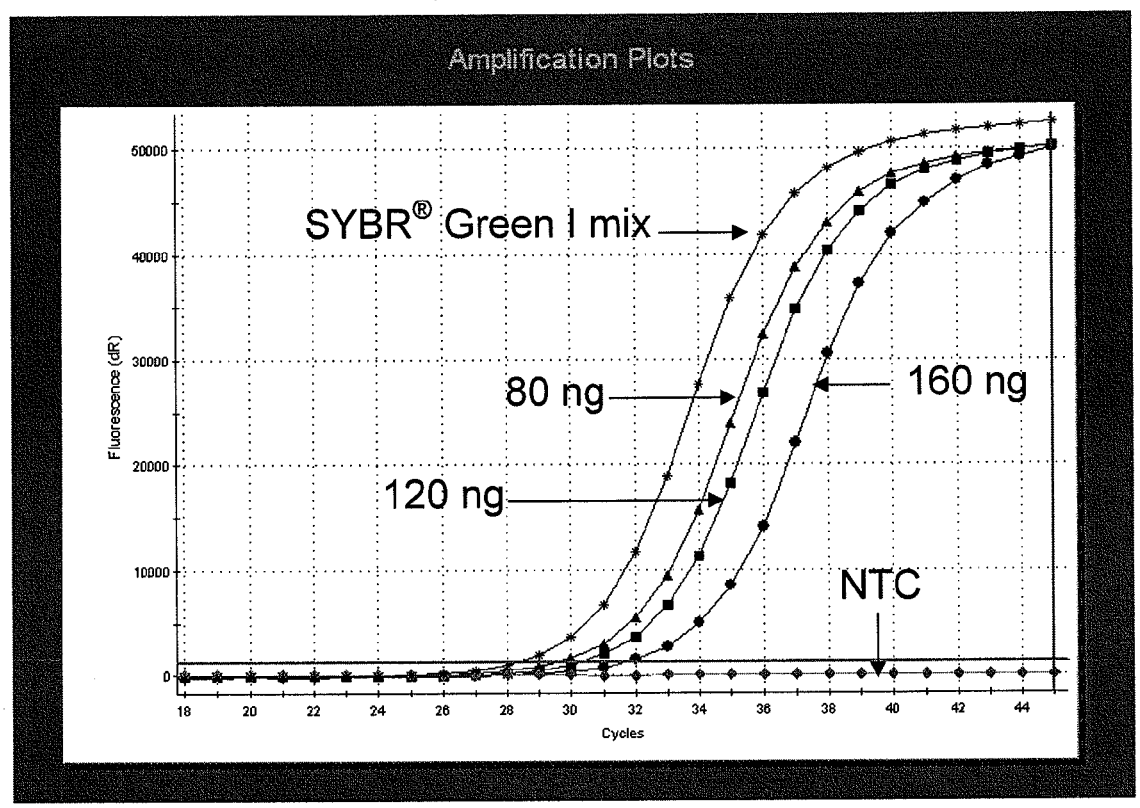
FIG. 6 shows quantitative real time polymerase chain reaction (qRT-PCR) data using V02-07027 dye

FIG. 6 shows the monitored fluorescent signal from the varying concentrations of the dye V02-07027 to optimize the amount of dye to be used when monitored using the 492/516 nm filter set. The increase in fluorescence after each cycle, for all the dye concentrations, followed the predicted shape of a typical real-time PCR amplification (that of a sigmoid curve)

and also resembled that observed from the amplification mixture containing SYBR® Green I. No increase in fluorescence was detected for the NTC reactions. Dye amounts greater than 80 ng inhibited PCR. No increase in fluorescence was detected when using any of the other monitored filter sets.

Figure 7:
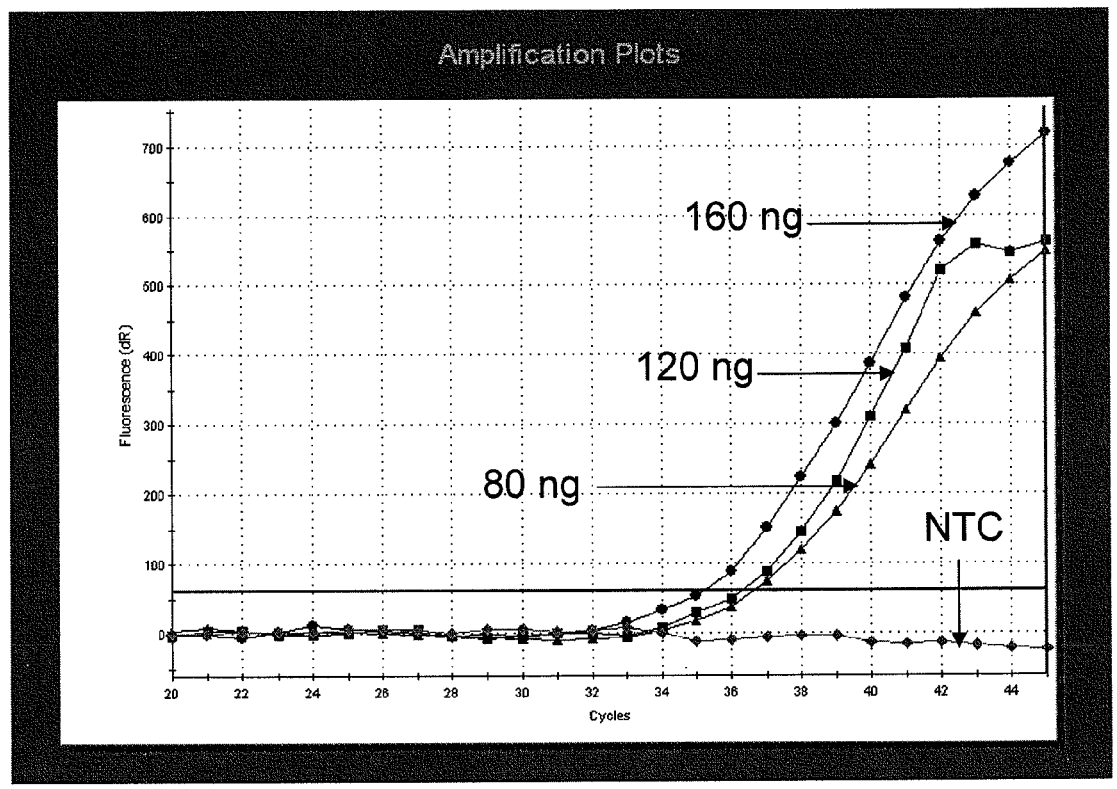
FIG. 7 shows qRT-PCR data using V02-07015 dye.

FIG. 7 shows the monitored fluorescent signal from varying concentrations of the dye V02-07015 when monitored using the 535/555 nm filter set. The increase in fluorescence after each cycle, for all the dye concentrations, followed the predicted shape of a typical real-time PCR amplification (that of a sigmoid curve). Amplification of product using the SYBR® Green I mixture was not detected when fluorescence was monitored in this wavelength. No increase in fluorescence was detected for the NTC reactions. No inhibition of PCR was observed with increasing amounts of dye. No increase in fluorescence was detected when using any of the other monitored filter sets.

Figure 8:
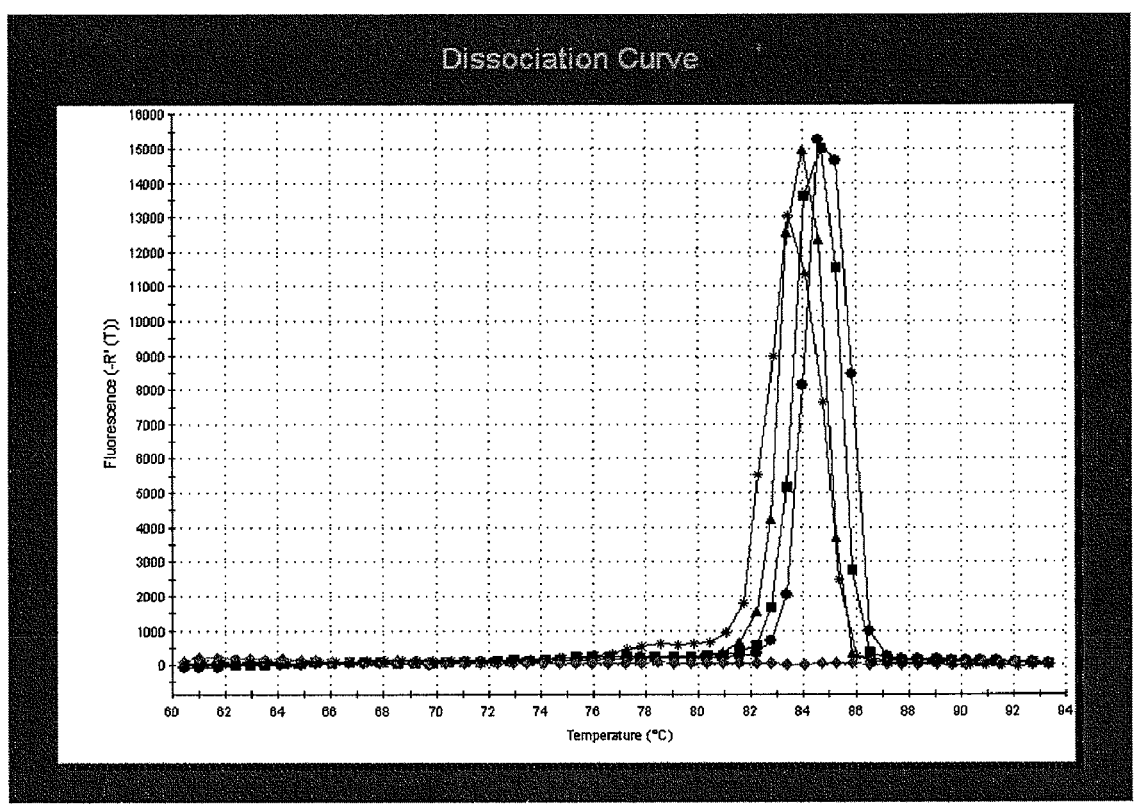
FIG. 8 shows data from a melting experiment with V02-07027 dye.

The disclosed dyes can also be used to confirm the presence of specific amplicon when using post-amplification melt curve analysis. As shown in FIG. 8, the derivative plot of the melt curve analysis, there was a single peak corresponding to a single amplicon produced during PCR. No peaks were observed in the NTC reactions.

Compound V02-07027 was also used to detect the formation of longer PCR amplicons using qRT-PCR: The following by fragments were used: 110 bp and 925 bp fragments from human β-actin gene, a 309 bp fragment from human Survivin gene, and a 413 bp fragment from human integrin α5 gene. Real time PCR was performed on a Stratagene® MX3000 (Stratagene, La Jolla Calif.) instrument using an excitation wavelength of 492 nm and an emission wavelength of 516 nm. Each amplification reaction (25 µl) contained 10 ng or 100 ng of human Genomic DNA, 200 µM of each dNTP, 1.5 mM $MgCl_2$, 50 mM KCL, 10 mM Tris-HCl, 400 nM of each of forward and reverse primers, and 2.5 units of Taq DNA polymerase (Thermo Fisher Scientific (Milwaukee Wis.)). Varying amounts of V02-07027 or a dye such as SYBR® Green (Invitrogen) were added to the reaction mix. Reactions were performed in triplicate and the data points represented the average signal.

The dye V02-07027, at concentrations ranging between 20 ng to 60 ng, bound to amplified DNA fragments, generating a fluorescent signal. The dye bound to varying lengths of amplicons (example 110 bp, 309 bp, 413 bp, and 925 bp) generating a fluorescent signal. The dye was able to bind to amplicons derived from varying amounts of the starting template (example, 10 ng, 100 ng). The dye could be used to measure the product of the amplification reaction based on the fluorescent signal generated upon dye binding to dsDNA. The increase in fluorescent signal during the PCR amplification corresponded to the increase in the amplified DNA that was generated in the reaction.

Detecting and quantifying small amounts of RNA is important in many determinations such as quantitating in vitro transcription yields and quantitating RNA concentration before performing RNA containing assays. RNA is typically quantitated by determining absorbance at 260 nm ($\lambda_{260}$), but disadvantages include protein interference, DNA absorbance, and the need for high concentration of RNA (>4 µg/ml). More sensitive fluorescence methods must be used to quantitate small amounts of RNA. A widely used RNA quantitation dye is RiboGreen® (Invitrogen), where 1 ng/ml of RNA can be detected and quantitated with a standard fluorometer, fluorescence microplate reader, or filter fluorometer.

In one embodiment, the inventive composition binds RNA. In one embodiment, compounds are provided that bind RNA in the absence of DNA. In one embodiment, the absence of DNA means substantially free of DNA and may be accomplished by methods known to a person of ordinary skill in the art such as treatment with a DNA nuclease. In one embodiment, the compounds exhibit increased fluorescence in the presence of RNA. In one embodiment, the compounds may be used to quantitate the amount of RNA present in a solution. For example, following the method of U.S. Patent Publication 20070072229, which is hereby incorporated by reference in its entirety, the resulting RNA may be quantitated using at least one of the present compounds. In one embodiment, at least one of compounds V11-03001, V11-02190, and V13-02162 exhibit affinity for RNA and may be used to detect and/or quantitate RNA.

Figure 9:
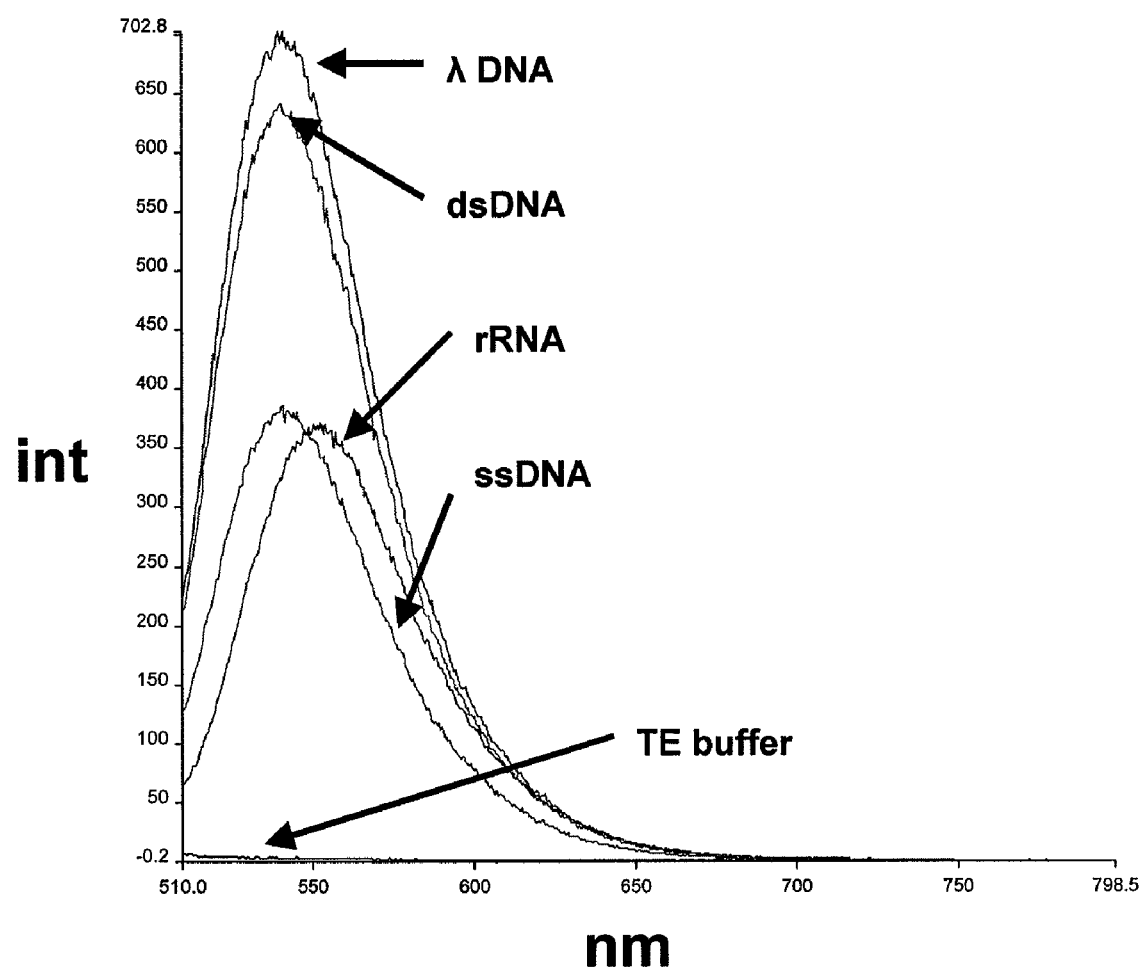
FIG. 9 shows fluorescence spectra of V11-03001 in the presence of DNA or RNA.
Figure 10:
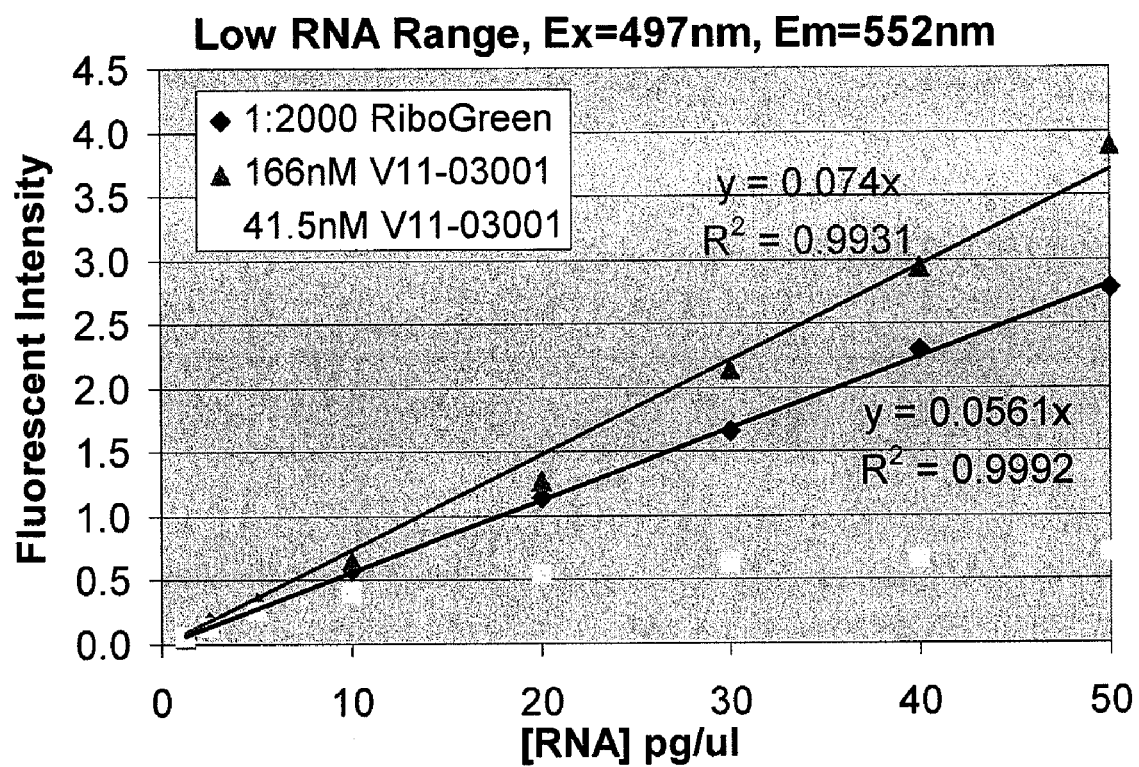
FIG. 10 shows low range RNA quantification using V11-03001.

In one embodiment, the V11-03001 compound may be used to quantitate RNA. The V11-03001 compound is not fluorescent by itself, as shown in FIG. 9, but in the presence of rRNA, the dye shows strong fluorescence with maximum emission at 552 nm ($\lambda_{552}$). The dye also shows fluorescence in the presence of DNA, however, the maximum for dye/DNA complex is shifted to 540 nm, as shown in FIG. 9. Additionally, with V11-03001 there was a linear relationship between fluorescence intensity and total RNA concentration in the low range RNA assay, as shown in FIG. 10. Fluorescence intensities were comparable to those using RiboGreen®.

In one embodiment, the dyes can be used in high resolution melting (HRM) curve analysis after qRT-PCR to verify, for example, that the desired product was amplified. In one embodiment, the dyes could be used to detect the presence of genetic variation, including heterozygous single base changes. Heteroduplex and homoduplex detection may be used for a variety of analyses, including mutation scanning and genotyping. Scanning is the process in which a nucleic acid fragment is compared to a reference nucleic acid fragment to detect the presence of any difference in sequence. A positive value indicates the presence of a sequence difference but may not necessarily reflect the exact nature of the sequence variance or its position on the nucleic acid fragment. Genotyping includes the detection and determination of known nucleic acid sequence variances, including but not limited to, SNPs, base deletions, base insertions, sequence duplications, rearrangements, inversions, base methylations, number of short tandem repeats; and in the case of a diploid genome, whether the genome is a homozygote or a heterozygote of the sequence variance, as well as the cis/trans positional relationship of two or more sequence variances on a DNA strand (haplotyping).

Single nucleotide polymorphisms (SNPs) are common genetic variations where a variation occurs only in a single base. The alteration may cause an amino acid change in a protein, alter rates of transcription, affect mRNA splicing, or have no apparent effect on cellular processes. In some cases, even if the change is silent (e.g., when the amino acid for which it codes does not change), SNP genotyping may still be valuable if the alteration is associated with a unique phenotype caused by another genetic alteration. Methods for genotyping SNPs include gel electrophoresis, mass spectrometry, and fluorescence. Fluorescence techniques that are homogeneous, and do not require adding reagents after commencement of amplification or physical sampling of the reactions for analysis are desirable.

High resolution melting is a rapid, high-throughput method for mutation scanning and genotyping, based on the melting point ($T_m$) DNA being inversely proportional to the hydrogen bonding strength of the constituent base pairs. Single base pair changes are detected by analyzing the shift in $T_m$ of the melting curves due to differences in hydrogen bonding strength. The amplicons are denatured and, using a highly sensitive optical detector, the dsDNA binding to one of the disclosed dyes is tracked by monitoring fluorescence across an accurately controlled temperature range. The resulting melting profiles can identify the presence of sequence variations within the amplicon.

In one embodiment, dyes used for HRM are saturation dyes. Saturation dyes are generally dyes that do not significantly inhibit PCR when present at concentrations that provide maximum fluorescence signal for an amount of dsDNA typically generated by PCR in the absence of dye. Although saturation dyes are identified by their compatibility with PCR at near saturating concentrations, it is understood that the dyes can be used at much lower concentrations. In embodiments, the dye can be added, e.g., after the PCR reaction. Thus, dyes that do inhibit PCR at or near saturating concentrations may be used.

Figure 11:
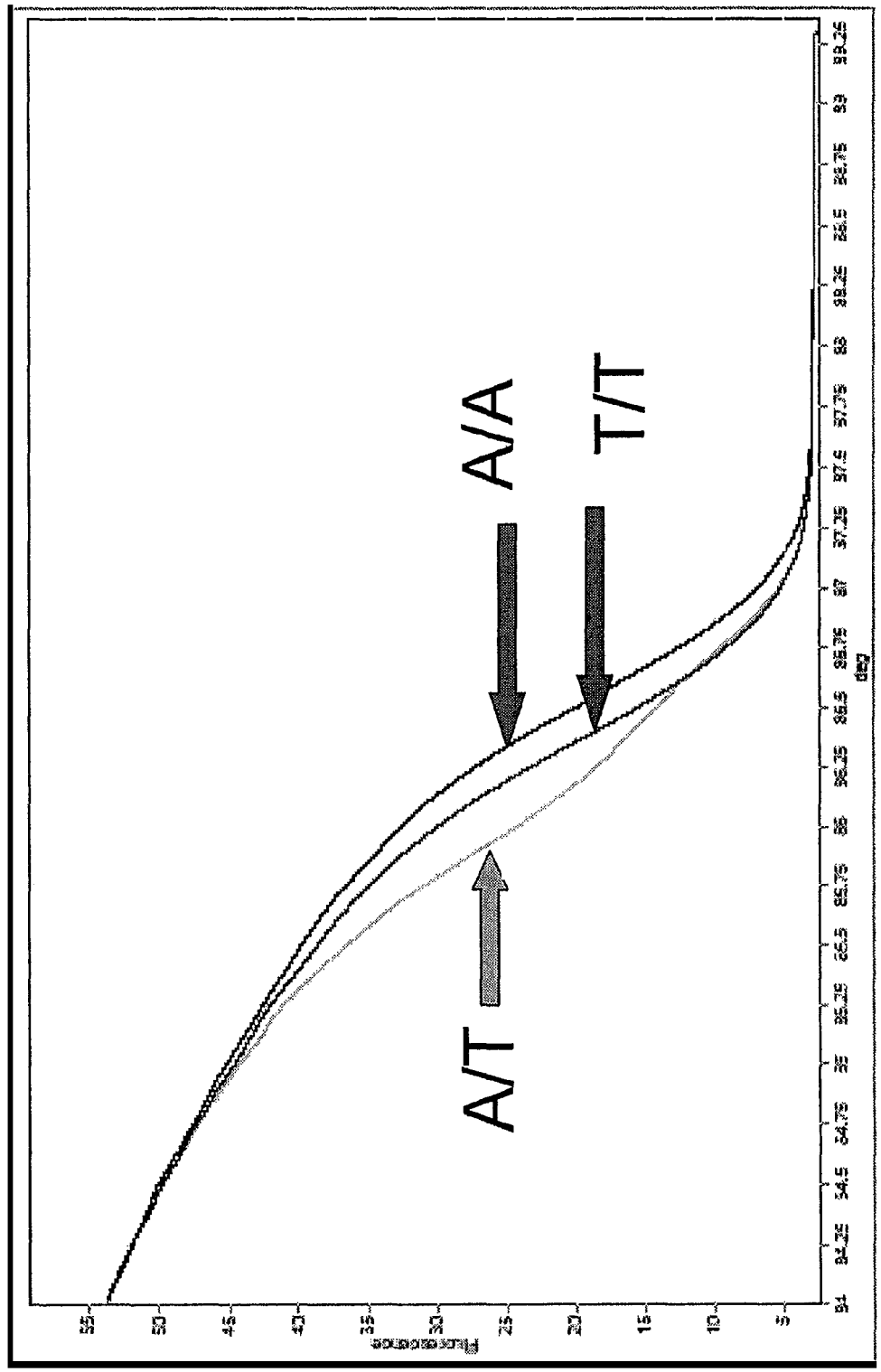
FIG. 11 shows high resolution screening data of a representative dye.
Figure 12:
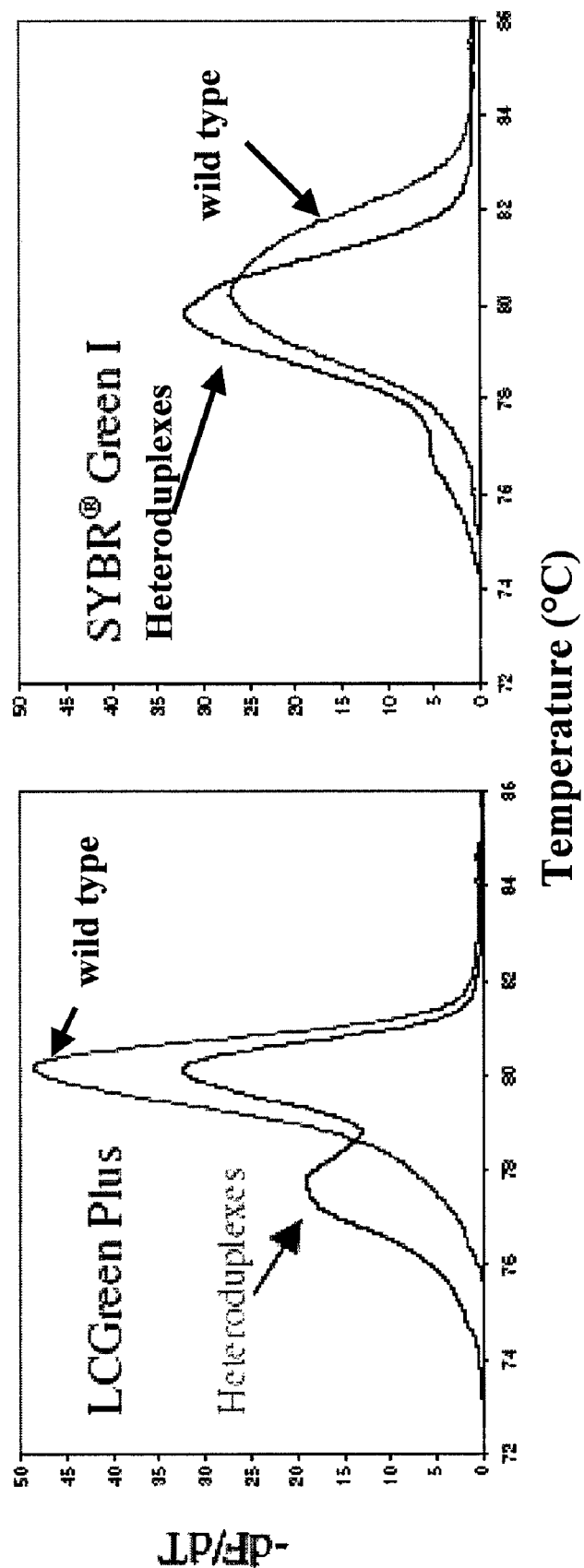
FIG. 12 shows high resolution melting curves with commercial dyes.

FIG. 11 shows a representative dye binding to three different DNA samples, permitting discrimination among single base pair changes among these DNA samples. FIG. 12 shows melting curves for wild type DNA and heterozygote mutant DNA treated with LCGreen® Plus or SYBR® Green I. The melting curves were analyzed by generating a derivative curve and analyzing the shape and location of one or more melting peaks on the derivative melting curve, as known to a person of ordinary skill in the art. The negative first derivative of the melting curve is plotted on the y axis, with temperature plotted on the x axis. Expressed in another way, a melting temperature profile may be graphically represented by plotting -dF/dT against T, where dF is the change in measured fluorescence emission, dT is the change in temperature of the nucleic acid, and T is the temperature of the nucleic acid. Such a graphic representation will show peaks at temperatures at which the most rapid changes in fluorescence occur, indicating melting temperatures. By accurately measuring the melting temperature, the presence of a heteroduplex, for example, created by a mutation, which would effect the melting temperature, is determined. The heteroduplex that is formed during PCR due to the heterozygous mutant was detected using LCGreen® Plus, but was not detected using SYBR® Green I. These results indicated that LCGreen® Plus had higher sensitivity than SYBR® Green I. Similar results are obtained using the disclosed dyes. In one embodiment, a method is provided that requires only a standard PCR mixture, including reagents such as a thermostable polymerase, such as Taq, and deoxyribonucleotide triphosphates (dNTPs), primers, and addition, prior to PCR, of one of the inventive dsDNA binding dyes. In one embodiment, scanning or genotyping is performed by melting curve analysis in the presence of one or more unlabeled probes and at least one of the disclosed double-stranded binding dyes. The melting curve analysis may take place during or subsequent to amplification, or in the absence of amplification. The dye may be at a saturating concentration.

In one embodiment, the dye may be added prior to PCR. When dye is added prior to a PCR reaction, it is often desirable that the dye does not interfere with the PCR reaction. In such embodiments, the dye may be a saturation dye. In one embodiment, the dye may be added after PCR. In such embodiments, a saturation dye and/or saturating concentrations of the dye need not necessarily be used.

While the disclosed dyes have been described in the context of real-time quantitative PCR analyses and melting curve analysis, it is understood that the inventive dyes may be used for a variety of methods such as nucleic acid quantitation, determination of initial nucleic acid concentration, testing for the presence of a nucleic acid, multiplexing with labeled probes, and other PCR-based methods.

In one embodiment, the disclosed dyes are used to label nucleic acids such as dsDNA in the nucleus of a cell. For example, the dyes can be used to label nucleic acids in samples that either contain, or are capable of containing, nucleic acids; such samples include, but are not limited to, cell lysate, tissue lysate, tissue culture, forensic samples, etc. When used to stain cells or tissues, the cells or tissues may be either live or fixed (e.g., histologically preserved). The sample was combined with the dye at an appropriate concentration and under appropriate conditions (e.g., temperature, pH, etc.) to evaluate fluorescence and hence to qualitatively detect the presence of nucleic acid in the sample. The concentration of nucleic acid in the sample may be quantitated by combining the sample with a biocompatible composition of the compound, incubating under conditions sufficient to result in a dye-nucleic acid complex yielding a detectable fluorescent signal, and quantitating nucleic acid by comparing fluorescence of the sample with fluorescence of a known quantity of nucleic acid.

In one embodiment, the disclosed dyes are used to specifically stain cell organelles. As one example, V02-06132 may be used as an RNA specific dye in cell organelles and may be used to monitor patterns and/or kinetics of gene expression and RNA transport. In one embodiment, the dye is reconstituted in dimethyl sulfoxide (DMSO) at about 1 mg/ml and then added to cells at a final concentration ranging from about 30 nM to about 1 μM. The cells are then incubated with the dye for a time and at a temperature that optimizes staining. In one embodiment, the cells may be incubated with the dye for about 15 minutes to about 1 hour at about 37° C. and then imaged. In one embodiment, the cells are first fixed and then subjected to staining with the dye. In one embodiment, the cells are fixed with 4% paraformaldehyde, washed, and then incubated with dye for 15 minutes, followed by cell imaging.

As one example, V02-07027 may be used as a DNA specific stain in cell organelles. It may be used to assess, e.g., DNA content, chromosome staining, localization, compartmentalization, cell proliferation, cell viability, cytotoxicity, etc. In one embodiment, the dye is reconstituted in DMSO at about 1 mg/ml and then added to the cells at a final concentration ranging from about 30 nM to about 1 μM. The cells are then incubated with the dye for a time and at a temperature that optimizes staining. In one embodiment, the cells may be incubated with the dye for about 15 minutes to about 1 hour at about 37° C. and then imaged. In one embodiment, the cells are first fixed and then subjected to staining with the dye. In one embodiment, the cells are fixed with 4% paraformaldehyde, washed, and then incubated with dye for 15 minutes, followed by cell imaging.

As other examples, V13-01026, V02-06136, and V02-06139 may be mitochondria specific stains and may be used, e.g., to track mitochondrial changes during apoptosis, investigate mitochondrial toxicity, uncoupling, anoxia, etc. Mitochondrial specific dyes may be combined with a mitochondrial membrane potential sensor and used to monitor effects of drugs on mitochondrial membrane potential. In one embodiment, the dye is reconstituted in DMSO at about 1 mg/ml and then added at a final concentration ranging from about 30 nM to about 1 μM to the cells. In one embodiment, the cells are incubated with dye at a concentration in the range of about 0.8 μM to about 2.5 μM. The cells are then incubated with the dye for a time period and at a temperature which optimizes staining. In one embodiment, the cells may be incubated with the dye for about 15 minutes to about 1 hour at about 37° C. and then imaged. In one embodiment, the cells are first fixed and then subjected to staining with the dye. In one embodiment, the cells are fixed with 4% paraformaldehyde, washed, and then incubated with dye for 15 minutes, followed by cell imaging.

As one example, V13-01035 may be a lysosome specific stain.

The embodiments and examples described are only illustrative and are not limiting in any way. As one example, the benzoxazole compound V02-06188 was tested and had a slight preference for binding to dsDNA over binding to ssRNA. Other benzoxazole compounds will likely also bind to dsDNA to a greater extent than will bind to ssDNA or RNA. As other examples, some aryl, oxazole, thiazole, 4-quinoline, 4-benzopyrylo, and 2-benzopyrylo compounds and dye compositions will likely bind to dsDNA to a greater extent that will bind to ssDNA or RNA. Therefore, various changes, modifications or alterations to these embodiments may be made without departing from the spirit of the invention and the scope of the following claims.

What is claimed is:

1. A compound of

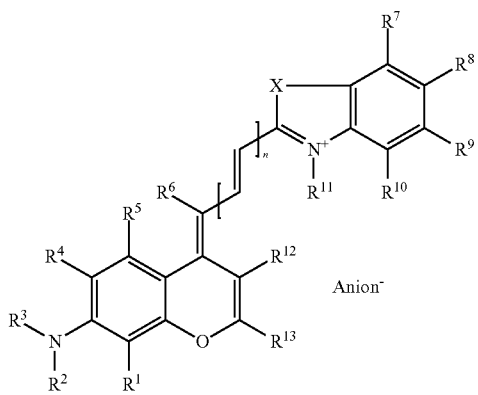

wherein
- each of $R^1$-$R^{10}$ and $R^{12}$ is independently H or a linear or branched hydrocarbon, optionally containing one or more heteroatoms;
- $R^1$ and $R^2$, $R^2$ and $R^3$, $R^3$ and $R^4$, $R^4$ and $R^5$, $R^7$ and $R^8$, $R^8$ and $R^9$, $R^9$ and $R^{10}$ or $R^6$ and $R^{12}$ are substituents capable of forming an aliphatic chain or ring, or an aromatic ring;
- $R^{11}$ is a linear or branched hydrocarbon, optionally containing one or more heteroatoms;
- $R^{13}$ is selected from
  - a linear, cyclic, or branched hydrocarbon that is saturated or unsaturated containing one or more heteroatoms, optionally containing a tetraalkylammonium group;
  - aryl or pyrimidyl; or
  - $NR^{14}R^{15}$ where $R^{14}$ and $R^{15}$ are the same or different and are independently H or a linear, cyclic, or branched hydrocarbon, with the proviso that if both R14 and R15 are hydrocarbon, at least one of R14 and R15 is containing one or more heteroatoms, optionally containing a tetraalkylammonium group, or $R^{14}$ and $R^{15}$ in combination complete a five, six, or seven membered saturated ring, optionally containing one or more heteroatoms optionally containing a quaternary ammonium group;
- X is S;
- n is an integer from 0 to 3; and anion⁻ is a counterion.

2. A composition comprising a compound of

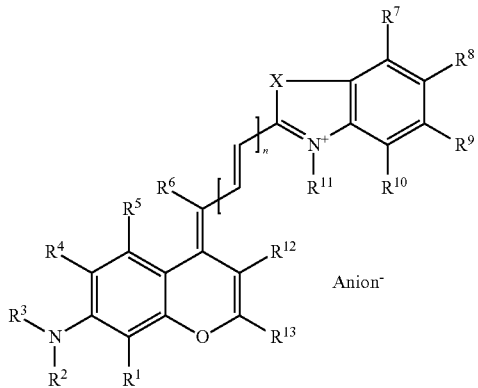

wherein
- each of $R^1$-$R^{10}$ and $R^{12}$ is independently H or a linear or branched hydrocarbon, optionally containing one or more heteroatoms;
- $R^1$ and $R^2$, $R^2$ and $R^3$, $R^3$ and $R^4$, $R^4$ and $R^5$, $R^7$ and $R^8$, $R^8$ and $R^9$, $R^9$ and $R^{10}$ or $R^6$ and $R^{12}$ are substituents capable of forming an aliphatic chain or ring, or an aromatic ring;
- $R^{11}$ is a linear or branched hydrocarbon, optionally containing one or more heteroatoms;
- $R^{13}$ is selected from
  - a linear, cyclic, or branched hydrocarbon that is saturated or unsaturated containing one or more heteroatoms, optionally containing a tetraalkylammonium group;
  - aryl or pyrimidyl; or
  - $NR^{14}R^{15}$ where $R^{14}$ and $R^{15}$ are the same or different and are independently H or a linear, cyclic, or branched hydrocarbon, with the proviso that if both R14 and R15 are hydrocarbon, at least one of R14 and R15 is containing one or more heteroatoms, optionally containing a tetraalkylammonium group, or $R^{14}$ and $R^{15}$ in combination complete a five, six, or seven membered saturated ring, optionally containing one or more heteroatoms optionally containing a quaternary ammonium group;
- X is S;
- n is an integer from 0 to 3; and anion⁻ is a counterion, and a biocompatible excipient.

3. The compound of claim 1 wherein the compound is selected from the group consisting of

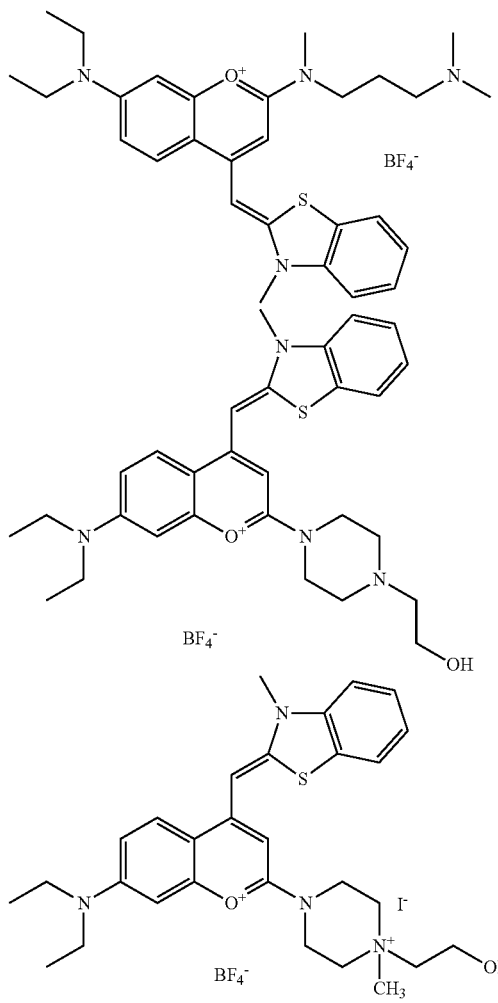

-continued

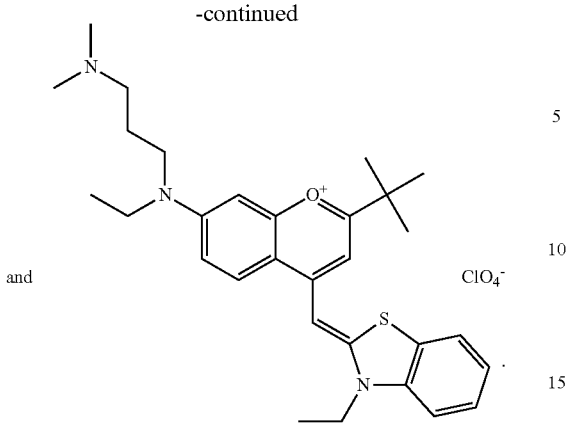

and

4. An method for detecting double stranded deoxyribonucleic acid (dsDNA), the method comprising,
providing a sample capable of containing dsDNA and a compound of

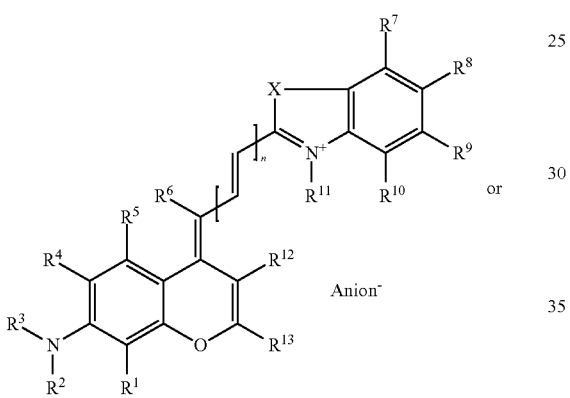

wherein
each of $R^1$-$R^{10}$ and $R^{12}$ is independently H or a linear or branched hydrocarbon, optionally containing one or more heteroatoms;
$R^1$ and $R^2$, $R^2$ and $R^3$, $R^3$ and $R^4$, $R^4$ and $R^5$, $R^7$ and $R^8$, $R^8$ and $R^9$, $R^9$ and $R^{10}$ or $R^6$ and $R^{12}$ are substituents capable of forming an aliphatic chain or ring, or an aromatic ring;
$R^{11}$ is a linear or branched hydrocarbon, optionally containing one or more heteroatoms;
$R^{13}$ is selected from
a linear, cyclic, or branched hydrocarbon that is saturated or unsaturated containing one or more heteroatoms, optionally containing a tetraalkylammonium group;
aryl or pyrimidyl; or
$NR^{14}R^{15}$ where $R^{14}$ and $R^{15}$ are the same or different and are independently H or a linear, cyclic, or branched hydrocarbon, with the proviso that if both R14 and R15 are hydrocarbon, at least one of R14 and R15 is containing one or more heteroatoms, optionally containing a tetraalkylammonium group, or $R^{14}$ and $R^{15}$ in combination complete a five, six, or seven membered saturated ring, optionally containing one or more heteroatoms optionally containing a quaternary ammonium group;
X is S;
n is an integer from 0 to 3; and anion⁻ is a counterion
under conditions sufficient for the compound to bind to dsDNA, and assaying the sample for fluorescence indicating binding of the compound to dsDNA.

5. The method claim 4 wherein the compound is selected from the group consisting of

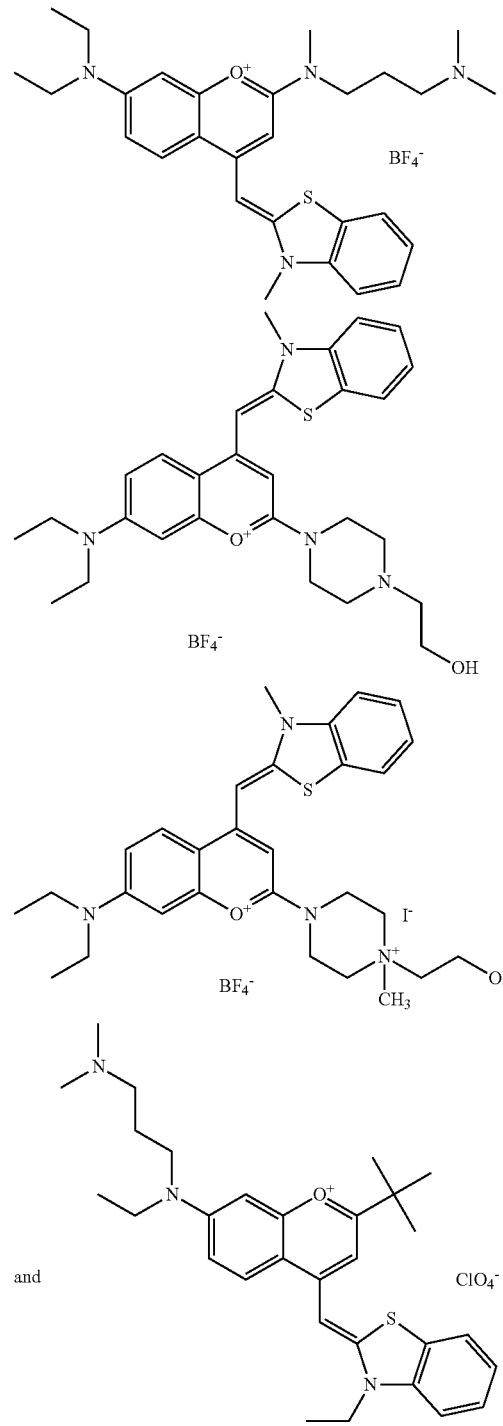

6. The method of claim 4 wherein quantitation of fluorescence in the sample quantitates dsDNA in the sample.

7. The method of claim 4 performed in a quantitative polymerase chain reaction (qPCR) or a real time polymerase chain reaction (qRT-PCR).

8. A method of quantitating nucleic acids in a sample, the method comprising
    combining a sample with the composition of claim 2,
    incubating the sample and composition under conditions sufficient for the compound to combine with the nucleic acid to form a dye-nucleic acid complex that yields a detectable fluorescent signal; and
    quantitating the nucleic acid in the sample by comparing the fluorescent signal with the signal from a known quantity of nucleic acid.

9. The method of claim 8 wherein the nucleic acid is double stranded deoxyribonucleic acid (dsDNA).

10. The method of claim 8 wherein the nucleic acid is ribonucleic acid (RNA).

11. A compound selected from the group consisting of

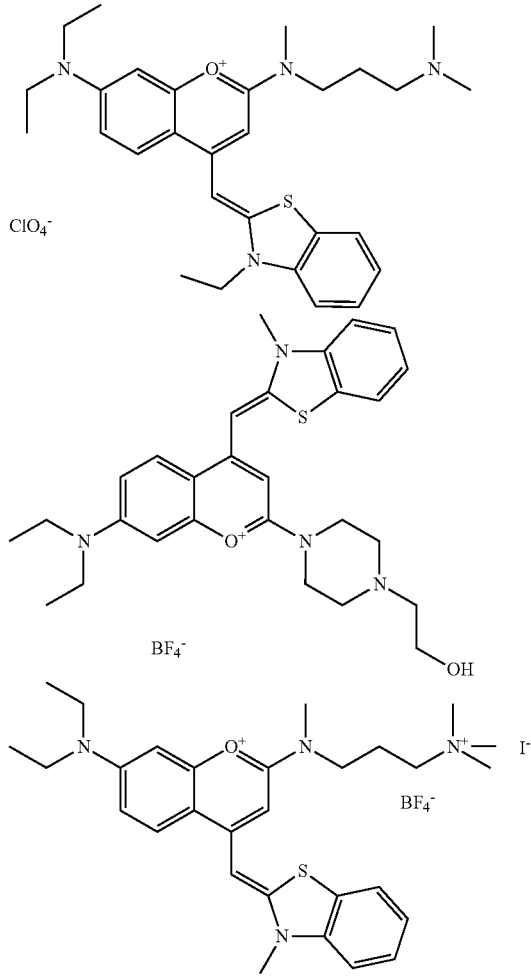

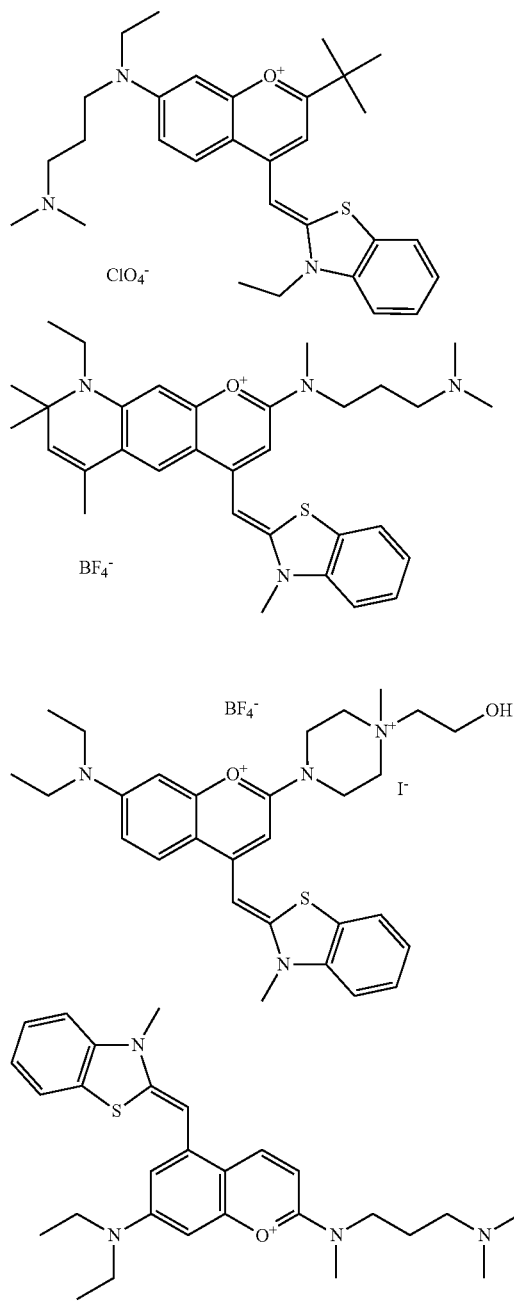

12. A composition comprising a compound having at least one of the structures of claim 11 and at least one biocompatible excipient.

* * * * *

UNITED STATES PATENT AND TRADEMARK OFFICE
CERTIFICATE OF CORRECTION

PATENT NO.        : 8,378,115 B2
APPLICATION NO.   : 12/680881
DATED             : February 19, 2013
INVENTOR(S)       : Charles K. Brush et al.

Page 1 of 1

It is certified that error appears in the above-identified patent and that said Letters Patent is hereby corrected as shown below:

- On the title page, Item (73) Assignee, reads: Thermo Fisher Scientific (Milwaukee) LLC", should read -- Thermo Fisher Scientific Inc. --

Signed and Sealed this
Fifteenth Day of October, 2013

Teresa Stanek Rea
*Deputy Director of the United States Patent and Trademark Office*

UNITED STATES PATENT AND TRADEMARK OFFICE
CERTIFICATE OF CORRECTION

PATENT NO.        : 8,378,115 B2                                                              Page 1 of 1
APPLICATION NO.   : 12/680881
DATED             : February 19, 2013
INVENTOR(S)       : Brush et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 191 days.

Signed and Sealed this
First Day of September, 2015

Michelle K. Lee
*Director of the United States Patent and Trademark Office*